United States Patent [19]
Ill et al.

[11] Patent Number: 5,744,326
[45] Date of Patent: Apr. 28, 1998

[54] USE OF VIRAL CIS-ACTING POST-TRANSCRIPTIONAL REGULATORY SEQUENCES TO INCREASE EXPRESSION OF INTRONLESS GENES CONTAINING NEAR-CONSENSUS SPLICE SITES

[75] Inventors: Charles R. Ill, Encinitas, Calif.; Scott Bidlingmaier, New Haven, Conn.

[73] Assignee: The Immune Response Corporation, Carlsbad, Calif.

[21] Appl. No.: 683,839

[22] Filed: Mar. 11, 1996

[51] Int. Cl.$^6$ ............... C12N 15/63; C12N 15/79; C07H 21/04
[52] U.S. Cl. ............... 435/172.3; 435/320.1; 536/24.1
[58] Field of Search ............... 435/69.1, 91.4, 435/172.3, 235.1, 320.1; 536/23.1, 24.1

[56] References Cited

U.S. PATENT DOCUMENTS 5,166,320  11/1992  Wu et al. ............... 530/395

OTHER PUBLICATIONS

Benitez, L.V. and J.E. Halver (1982), "Ascorbic acid sulfate sulfohydrolase (C$_2$ sulfatase): The modulator of cellular levels of L-ascorbic acid in rainbow trout", *Proc. Natl. Acad. Sci. USA* 79:5445–5449.

"Drug Facts and Comparisons", 1992 Edition, eds. Olin, B.R. et al., St. Louis, MO, pp. 2445–2460.

Huang, J. and T.J. Liang (1993), "A Novel Hepatitis B Virus (HBV) Genetic Element with Rev Response Element–Like Properties That Is Essential for Expression of HBV Gene Products", *Mol. and Cell. Biol.* 13:7476–7486.

Huang, Z–M. and T.S.B. Yen (1994), "Hepatitis B Virus RNA Element That Facilitates Accumulation of Surface Gene Transcripts in the Cytoplasm", *J. Virol.* 68:3193–3199.

Huang, Z–M. and T.S.B. Yen (1995), "Role of the Hepatitis B Virus Posttransitional Regulatory Element in Export of Intronless Transcripts", *Mol. and Cell. Biol.* 15:3864–3869.

Huang, Z–M. et al. (1996), "Cellular Proteins That Bind to the Hepatitis B Virus Posttransitional Regulatory Element", *Virology* 217:573–581.

Wu, C.H. et al. (1989), "Targeting Genes: Delivery and Persistent Expression of a Foreign Gene Driven by Mammalian Regulatory Elements in Vivo", *J. Biol. Chem.* 264:16985–16987.

Wu, G.Y. and C.H. Wu (1987), "Receptor–mediated in Vitro Gene Transformation by a Soluble DNA Carrier System", *J. Biol. Chem.* 262:4429–4432.

Wu, G.Y. and C.H. Wu (1988), "Receptor–mediated Gene Delivery and Expression in Vivo", *J. Biol. Chem.* 263:14621–14624.

Liu and Mertz. HnRNP L binds a cis–acitng RNA sequence element that enables intron–independent bene expression. Genes and Dev. vol., 9:1766–1780, Aug. 2, 1995.

*Primary Examiner*—David Guzo
*Assistant Examiner*—William Sandals
*Attorney, Agent, or Firm*—Lahive & Cockfield, LLP; Jane E. Remillard

[57] ABSTRACT

Expression vectors are disclosed comprising intronless genes containing one or more near consensus splice sequences and one or more copies of a viral cis-acting post-transcriptional regulatory element which is transcribed along with the gene and causes export of the gene transcript from the nucleus into the cytoplasm of the cell. In a preferred embodiment, the vectors are targeted for delivery to specific cells in the form of a molecular complex made up of the plasmid releasably linked to a nucleic acid binding agent and a ligand which binds to a component on the surface of a cell. Use of viral cis-acting post-transcriptional regulatory elements as disclosed can increase expression of intronless genes with near-consensus splice sites.

15 Claims, 10 Drawing Sheets

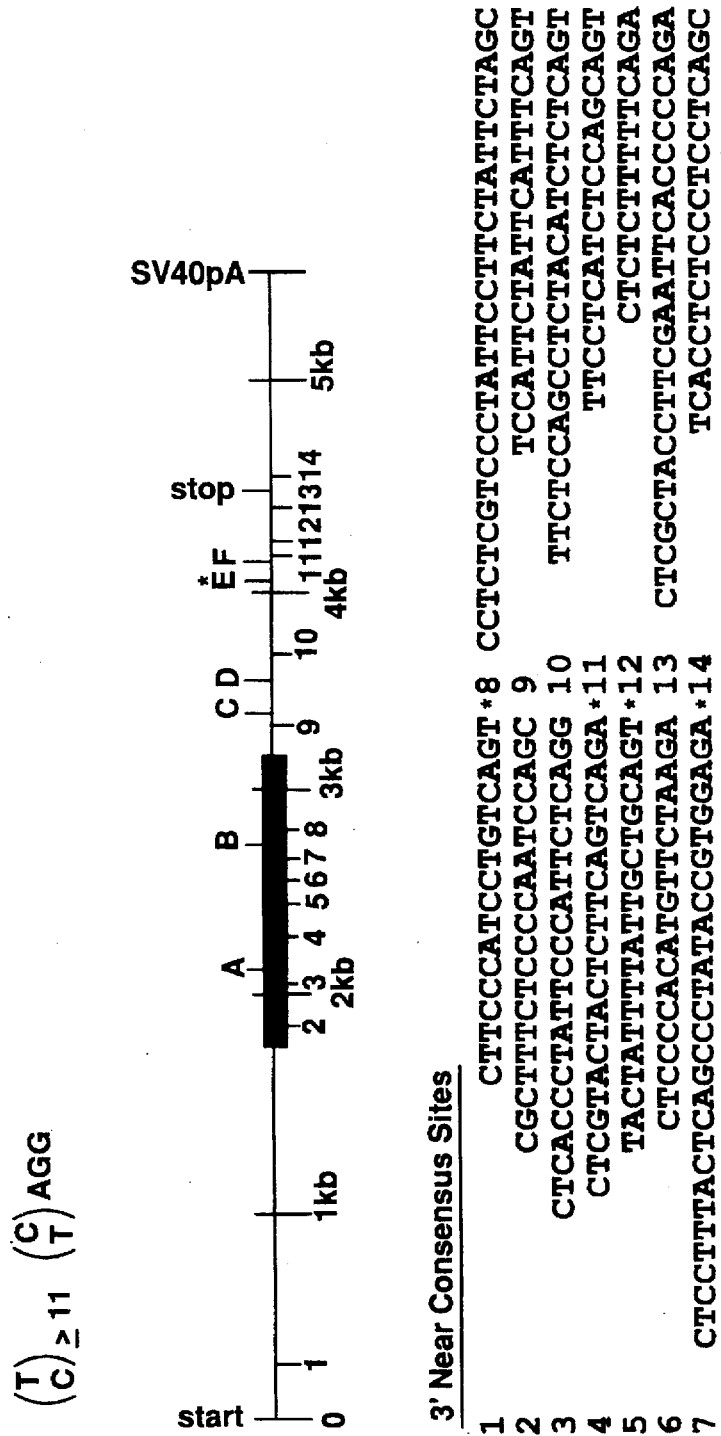

PRE of HBV

Normalized Values of Factor VIII RNA

|  | FVIII/GAPDH |
|---|---|
| Lane 1 = LA 3-5 BDD-FVIII | 1.753 |
| Lane 2 = pMT2LA8 | 1.603 |
| Lane 3 = pcDNAF8dK (intron only) | 0.775 |
| Lane 4 = pcF8dKPREdSV (PRE, no intron) | 3.694 |
| Lane 5 = pcF8dKSVPRE (intron and PRE) | 1.269 |
| Lane 6 = HUH-7 (Human Liver Carcinoma) | 0.245 |

25ug F8 Plasmids Transfected Via Calcium Phosphate
+ 25ng CMVHGH(Transfection normalization)

USE OF VIRAL CIS-ACTING POST-TRANSCRIPTIONAL REGULATORY SEQUENCES TO INCREASE EXPRESSION OF INTRONLESS GENES CONTAINING NEAR-CONSENSUS SPLICE SITES

BACKGROUND OF THE INVENTION

It has been shown that several viruses which replicate via reverse transcription rely on certain regulatory sequences to regulate the transport of unspliced and partially spliced transcripts into the cytoplasm where they are expressed as viral proteins. For example, the retrovirus, HIV-1, relies on a Rev-response element (RRE), in addition to a Rev protein, to direct export of certain transcripts from the cell nucleus into the cytoplasm, thereby facilitating their expression (See e.g., Cullen et al. (1991) *Science* 16: 346–350; and Rosen et al. (1990) *AIDS* 4: 499–509).

Hepatitis B virus (HBV) is another virus which undergoes reverse transcription during its replication cycle and relies on cis-acting elements to regulate cytoplasmic accumulation of gene transcripts. In particular, all of the known protein products of HBV are encoded on one strand of the circular genome, and are translated from unspliced transcripts. It has been shown that a region encompassing enhancer II and located downstream of the surface gene coding region within surface gene transcripts, named the post-transcriptional regulatory element (PRE), acts in cis at the RNA level to allow transport of these HBV transcripts from the nucleus to the cytoplasm without any effects on transcriptional initiation or cytoplasmic RNA stability (see e.g., Huang et al. (1995) *Molec. and Cell. Biol.* 15(7): 3864–3869; Huang et al. (1994) *J. Virol.* 68(5): 3193–3199; Huang et al. (1993) *Molec. and Cell. Biol.* 13(12): 7476–7486). The effect of relocation of the PRE sequence to a position downstream of the surface gene transcription termination site is a greater than four-fold reduction in the number of cytoplasmic surface gene transcripts, but not of nuclear gene transcripts Huang et al. (1994), supra.

It has been suggested by Huang et al. (1995), supra, that the function of the PRE during the HBV life cycle is to allow the export of HBV surface gene transcripts into the cytoplasm without these transcripts being spliced. The authors further suggest that the PRE may represent one example of a class of RNA cis elements that activate expression of naturally intronless genes of higher eucaryotes by allowing the export of their transcripts into the cytoplasm.

SUMMARY OF THE INVENTION

The present invention provides a method for increasing expression of an intronless gene containing one or more near-consensus splice sites by operably (i.e., functionally) linking one or more copies of a viral cis-acting post-transcriptional regulatory element (PRE) to the gene so that it is transcribed along with the gene and causes export of the gene transcript from the nucleus into the cytoplasm of the cell. In one embodiment, the PRE sequence is linked to the gene at a position which is 3' of the stop signal and 5' of the polyadenylation signal.

The present invention further provides an expression plasmid comprising (a) an intronless gene containing one or more near consensus splice sequences operably linked to a promoter sequence so that the gene is transcribed in a cell, and (b) one or more copies of a viral cis-acting post-transcriptional regulatory element (PRE) which is transcribed along with the gene and causes export of the gene transcript from the nucleus into the cytoplasm of the cell.

In one embodiment, the PRE is derived from hepatitis B virus. A preferred PRE of HBV comprises a nucleotide sequence of SEQ ID NO: 1.

In another embodiment, the intronless gene (e.g., a cDNA) containing one or more near consensus splice sequences encodes a blood coagulation factor, such as Factor VIII or Factor IX.

The expression plasmid can be transfected into cells either in vitro or in vivo to obtain increased expression of the intronless gene relative to expression obtained in the absence of a PRE sequence. In a preferred embodiment, the expression plasmid is targeted for delivery to a specific cell by forming a molecular complex of the plasmid and a conjugate made up of a nucleic acid binding agent (e.g., a polycation) and a ligand which binds to a component on the surface of the cell. In one embodiment, the ligand binds to the asialoglycoprotein receptor present on hepatocytes.

BRIEF DESCRIPTION OF THE FIGURES

FIG. 1 shows (a) human B-domain deleted Factor VIII cDNA 5' and 3' junction near-consensus splicing sequences (SEQ ID NOS: 4–17), as well as a map of where these near-consensus sequences are located within the human B-domain deleted Factor VIII cDNA.

DETAILED DESCRIPTION OF THE INVENTION

The present invention pertains to the use of a viral cis-acting post-transcriptional regulatory elements or "PRE"

to increase expression of intronless genes containing one or more near-consensus splice sites. The PRE sequence is linked to the intronless gene (e.g., in an appropriate expression vector) so that it (a) is transcribed along with the gene and, therefore, is present in the gene transcript, and so that it (b) retains its function as a cis-acting sequence which directs the transport of the gene transcript out of the cell nucleus into the cytoplasm where it is expressed. Linkage of the gene and the PRE in this manner will hereafter be referred to as "operable" linkage.

I. VIRAL "PRE" SEQUENCES

The term "viral cis-acting post-transcriptional regulatory element" or "PRE", as used herein", refers to a viral sequence which acts in cis at the post-transcriptional level (i.e., within a gene transcript) to increase cytoplasmic accumulation of unspliced gene transcripts (i.e., which contain no introns) and contain one or more near-consensus splice sites. An increase in cytoplasmic accumulation of the gene transcript is measured relative to levels obtained in the absence of a PRE sequence.

PRE sequences are commonly found in viruses which replicate via reverse transcription, particularly viruses whose protein products are translated from unspliced transcripts. These sequences regulate the transport of the unspliced viral transcripts from the cell nucleus to the cytoplasm where they are expressed. Examples of viruses for which PRE sequences have been identified include retroviruses, such as human and feline immunodeficiency virus (HIV and FIV) (see e.g., Cullen et al. (1991) *J. Virol.* 65: 1053; and Cullen et al. (1991) *Cell* 58: 423–426), and hepatitis B virus (see e.g., Huang et al. (1995) *Molec. and Cell Biol.* 15(7): 3864–3869; Huang et al. (1994) *J. Virol.* 68(5): 3193–3199, Huang et al. (1993) *Molec. and Cell. Biol.* 13(12): 7476–7486).

Figure 9:
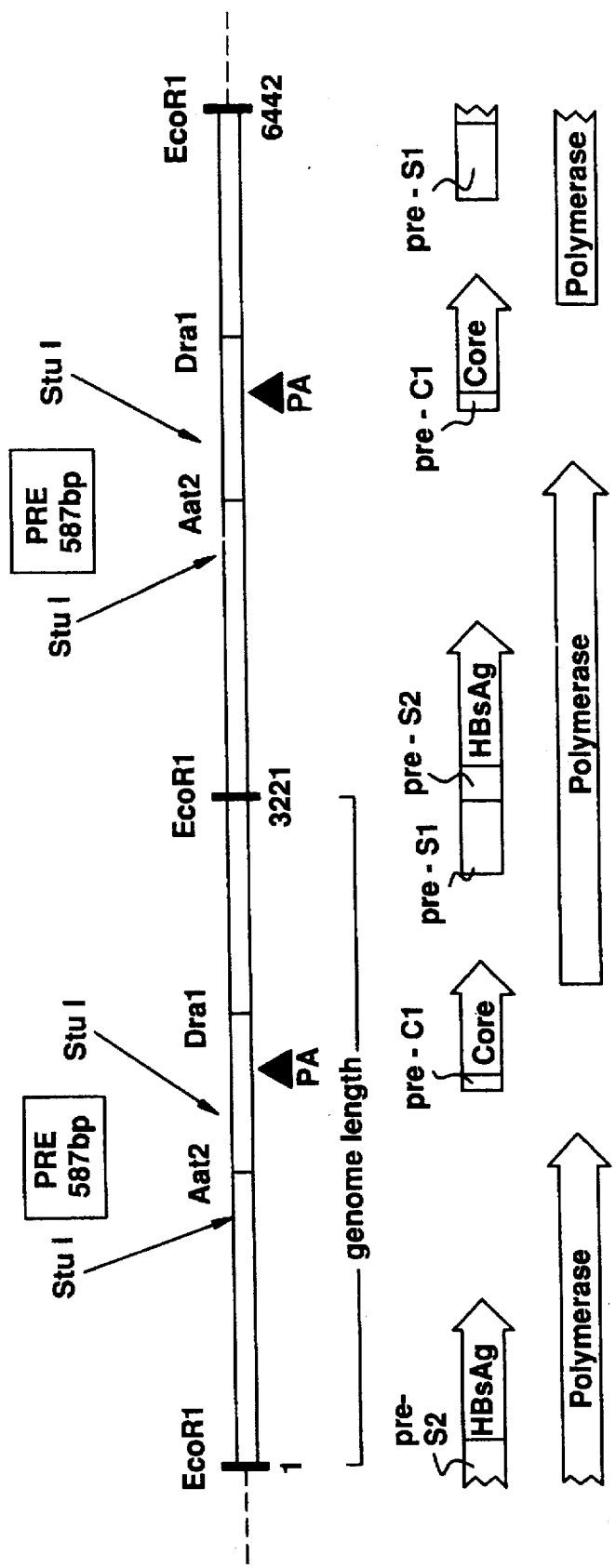
FIG. 9 shows a map of the HBV genome and the location of the PRE sequence within the genome.

In one embodiment of the invention, the PRE is derived from hepatitis B virus (HBV). A preferred PRE of HBV is a sequence of approximately 587 nucleotides (SEQ ID NO: 1) which encompasses enhancer II and is within the transcribed portion of the surface antigen gene (see FIG. 9). This PRE sequence has been shown to function in cis to increase the steady-state levels of surface gene transcripts by facilitating cytoplasmic accumulation of these transcripts.

II. INTRONLESS GENES

Appropriate genes for use in the invention include any intronless gene which contains one or more near-consensus splice sites, as defined herein. The term "intronless gene", as used herein, refers to a gene which encodes an mRNA which is translated without having been spliced. Such genes generally contain no consensus 3' donor or 5' acceptor splice sites.

In all cases the gene must be in a form suitable for expression by a cell and is generally contained in an appropriate vector (e.g., an expression vector), such as a plasmid. For example, the intronless gene must be operably linked to appropriate genetic regulatory elements which are functional in the target cell. Such regulatory sequences include, for example, promoter sequences which drive transcription of the gene. Suitable promoters include a broad variety of viral promoters, such as SV40 and CMV promoters. The intronless gene may also include appropriate signal sequences which provide for trafficking of the encoded protein to intracellular destinations and/or extracellular secretion. The signal sequence may be a natural sequence of the protein or an exogenous sequence.

Regulatory sequences required for gene expression, processing and secretion are art-recognized and are selected to direct expression of the desired protein in an appropriate cell. Accordingly, the term "regulatory sequence", as used herein, includes promoters, enhancers and other expression control elements. Such regulatory sequences are known and discussed in Goeddel, *Gene expression Technology: Methods in Enzymology*, p. 185, Academic Press, San Diego, Calif. (1990).

One class of intronless genes (which can contain near-consensus splice sites) which can be used in the present invention are cDNAs. cDNAs are generally reverse transcribed from mRNAs which have already been spliced and, as a result, do not typically contain introns, although exogenous introns (e.g., viral intervening (IVS) sequences) may be subsequently added. cDNAs which exhibit low levels of expression likely contain one or more near-consensus splice sites and, therefore, are highly appropriate for use in the present invention.

The intronless gene can encode any desired protein (e.g., having therapeutic or diagnostic value). In one embodiment, the intronless gene (e.g., a cDNA) encodes all or a portion of a blood coagulation factor, (or a variant, analog or modified version (e.g., chimeric protein) thereof). For example, the gene can encode human B-domain deleted Factor VIII (bases 2965 to 7377 of SEQ ID NO. 2) which contains at least 6 near-consensus 5' (donor) splice sites having 6–7 out of 9 bases identical to the 5'(A/C)AG GT(A/G)AGT consensus splice sequence (see FIG. 1). In addition, the B-domain deleted cDNA contains at least 14 near-consensus 3' (acceptor) splice sites (SEQ ID NOS: 4–17) (see FIG. 1). This B-domain deleted Factor VIII sequence exhibits low levels of expression compared to cDNAs for other genes. However, as demonstrated in the following examples, low expression of B-domain deleted Factor VIII cDNA can be significantly increased by operably linking the gene to a PRE sequence.

Another example of an intronless gene encoding a blood coagulation factor for which near-consensus splice sequences have been identified is a cDNA encoding Factor IX (see e.g., Yull et al. (1995) *PNAS* 92: 10899–10903).

III. "NEAR-CONSENSUS" SPLICE SITES

Intronless genes of the invention contain one or more near-consensus splice sites. The term "near-consensus splice site", as used herein, refers to nucleotide sequences which differ from consensus splice (5' donor or 3' acceptor) sequences (see FIG. 1) by the addition, deletion, or substitution of one or more nucleotides. Preferably, the near-consensus splice site is greater than 50%, and more preferably about 70–80%, homologous to consensus 5' and 3' splice sequences. It is believed that this level of homology makes the near-consensus sequence recognizable to cellular spliceosomes which look for and bind to consensus 3' and 5' splice sites. As a result, intronless gene transcripts containing near-consensus splice sequences are believed to get tied up in the nucleus of the cell where splicing occurs, rather than being transported to the cytoplasm where they can be translated to proteins.

Cellular splicing of gene transcripts involves the binding of a spliceosome to a 5' (donor) splice site having the following consensus sequence: (A/C)AG<u>GT</u>(A/G)AGT. The spliceosome then scans in the 3' direction for a branch point sequence, followed by a 3' (acceptor) splice site having the following consensus sequence: (T/C) . . . ≧11 (pyrimidine track) . . . (C/T)<u>AG</u>G. Once this 3' splice site is found, the spliceosome will then cleave the transcript 5' of the GT at the 5' donor splice site and 3' of the AG at the 3' acceptor site.

Accordingly, genes containing one or more near-consensus splice sites can be identified by analyzing their nucleotide sequences for the presence of sequences which are highly homologous (e.g., more than 50–90% homologous) to the 3' and 5' consensus sequences disclosed above. In general, genes containing such near-consensus splice sites, with no consensus splice sites (i.e., no introns), will exhibit low levels of protein expression because their transcripts are not efficiently transported to the cytoplasm. However, this low level of expression can generally be corrected (i.e., increased) by linking a viral PRE sequence to the gene, as described herein.

IV. OPERABLY LINKING PRE SEQUENCES TO INTRONLESS GENES CONTAINING NEAR-CONSENSUS SPLICE SITES

The viral PRE of the invention is operably linked to the intronless gene, for example, in an expression vector, so that it (a) is transcribed along with the gene and, therefore, is present in the gene transcript, and so that it (b) retains its function as a cis-acting sequence which directs the transport of the gene transcript out of the cell nucleus into the cytoplasm where it is expressed. The expression vector can be any vector which contains the appropriate genetic regulatory elements required for expression of the gene, such as those previously described (e.g., promoter and enhancer elements). Such expression vectors are well known in the art and can be purchased from commercially available sources.

In one embodiment, the PRE is linked to the gene at a position downstream of the stop codon of the gene (i.e., in the untranslated region), and upstream of the polyadenylation signal (i.e., in the transcribed region). The PRE may also be linked to the gene at a position which is upstream of the start codon and which does not interfere with translation of the gene (e.g., preferably not within the leader sequence). The PRE sequence may be linked to the gene as one or as multiple (i.e., two or more) copies.

V. GENE DELIVERY AND EXPRESSION

Following linkage in an appropriate expression plasmid of one or more viral PRE sequences to an intronless gene containing one or more near-consensus splice sites, as described herein, the plasmid can be delivered to cells either in vitro or in vivo. For example, the plasmid can be transfected into cells in vitro using standard transfection techniques, such as calcium phosphate precipitation. Alternatively, the plasmid can be delivered to cells in vivo by, for example, intravenous or intramuscular injection.

In a preferred embodiment of the invention, the expression plasmid is targeted for delivery to a specific cell by releasably linking the plasmid to a carrier molecule made up of a nucleic acid binding agent and a ligand which binds to a component on the surface of a cell, thereby forming a polynucleotide-carrier complex.

The carrier molecule of the polynucleotide-carrier complex performs at least two functions: (1) it binds the polynucleotide (e.g., the plasmid) in a manner which is sufficiently stable (either in vivo, ex vivo, or in vitro) to prevent significant uncoupling of the polynucleotide extracellularly prior to internalization by a target cell, and (2) it binds to a component on the surface of a target cell so that the polynucleotide-carrier complex is internalized by the cell. Generally, the carrier is made up of a cell-specific ligand and a cationic moiety which, for example are conjugated. The cell-specific ligand binds to a cell surface component, such as a protein, polypeptide, carbohydrate, lipid or combination thereof. It typically binds to a cell surface receptor. The cationic moiety binds, e.g., electrostatically, to the polynucleotide.

The ligand of the carrier molecule can be any natural or synthetic ligand which binds a cell surface receptor. The ligand can be a protein, polypeptide, glycoprotein, glycopeptide or glycolipid which has functional groups that are exposed sufficiently to be recognized by the cell surface component. It can also be a component of a biological organism such as a virus, cells (e.g., mammalian, bacterial, protozoan).

Alternatively, the ligand can comprise an antibody, antibody fragment (e.g., an F(ab')$_2$ fragment) or analogues thereof (e.g., single chain antibodies) which binds the cell surface component (see e.g., Chen et al. (1994) *FEBS Letters* 338:167–169, Ferkol et al. (1993) *J. Clin. Invest.* 92:2394–2400, and Rojanasakul et al. (1994) *Pharmaceutical Res.* 11(12):1731–1736). Such antibodies can be produced by standard procedures.

Ligands useful in forming the carrier will vary according to the particular cell to be targeted. For targeting hepatocytes, proteins and polypeptides containing galactose-terminal carbohydrates, such as carbohydrate trees obtained from natural glycoproteins, can be used. For example, natural glycoproteins that either contain terminal galactose residues or can be enzymatically treated to expose terminal galactose residues (e.g., by chemical or enzymatic desialylation) can be used. In one embodiment, the ligand is an asialoglycoprotein, such as asialoorosomucoid, asialofetuin or desialylated vesicular stomatitis virus.

Alternatively, suitable ligands for targeting hepatocytes can be prepared by chemically coupling galactose-terminal carbohydrates (e.g., galactose, mannose, lactose, arabinogalactan etc.) to nongalactose-bearing proteins or polypeptides (e.g., polycations) by, for example, reductive lactosamination. Methods of forming a broad variety of other synthetic glycoproteins having exposed terminal galactose residues, all of which can be used to target hepatocytes, are described, for example, by Chen et al. (1994) *Human Gene Therapy* 5:429–435 and Ferkol et al. (1993) *FASEB* 7: 1081–1091 (galactosylation of polycationic histones and albumins using EDC); Perales et al. (1994) *PNAS* 91:4086–4090 and Midoux et al. (1993) *Nucleic Acids Research* 21(4):871–878 (lactosylation and galactosylation of polylysine using α-D-galactopyranosyl phenylisothiocyanate and 4-isothiocyanatophenyl β-D-lactoside); Martinez-Fong (1994) *Hepatology* 20(6):1602–1608 (lactosylation of polylysine using sodium cyanoborohydride and preparation of asialofetuin-polylysine conjugates using SPDP); and Plank et al. (1992) *Bioconjugate Chem.* 3:533–539 (reductive coupling of four terminal galactose residues to a synthetic carrier peptide, followed by linking the carrier to polylysine using SPDP).

For targeting the polynucleotide-carrier complex to other cell surface receptors, the carrier component of the complex can comprise other types of ligands. For example, mannose can be used to target macrophages (lymphoma) and Kupffer cells, mannose 6-phosphate glycoproteins can be used to target fibroblasts (fibro-sarcoma), intrinsic factor-vitamin B12 and bile acids (See Kramer et al. (1992) *J. Biol. Chem.* 267:18598–18604) can be used to target enterocytes, insulin can be used to target fat cells and muscle cells (see e.g., Rosenkranz et al. (1992) *Experimental Cell Research* 199:323–329 and Huckett et al. (1990) *Chemical Pharma-* cology 40(2):253–263), transferrin can be used to target smooth muscle cells (see e.g., Wagner et al. (1990) *PNAS* 87:3410–3414 and U.S. Pat. No. 5,354,844 (Beug et al.)), Apolipoprotein E can be used to target nerve cells, and pulmonary surfactants, such as Protein A, can be used to target epithelial cells (see e.g., Ross et al. (1995) *Human Gene Therapy* 6:31–40).

The cationic moiety of the carrier molecule can be any positively charged species capable of electrostatically binding to negatively charged polynucleotides. Preferred cationic moieties for use in the carrier are polycations, such as polylysine (e.g., poly-L-lysine), polyarginine, polyornithine, spermine, basic proteins such as histones (Chen et al., supra.), avidin, protamines (see e.g., Wagner et al., supra.), modified albumin (i.e., N-acylurea albumin) (see e.g., Huckett et al., supra.) and polyamidoamine cascade polymers (see e.g., Haensler et al. (1993) *Bioconjugate Chem.* 4: 372–379). A preferred polycation is polylysine (e.g., ranging from 3,800 to 60,000 daltons).

In one embodiment, the carrier comprises polylysine having a molecular weight of about 17,000 daltons (purchased as the hydrogen bromide salt having a MW of a 26,000 daltons), corresponding to a chain length of approximately 100–120 lysine residues. In another embodiment, the carrier comprises a polycation having a molecular weight of about 2,600 daltons (purchased as the hydrogen bromide salt having a MW of a 4,000 daltons), corresponding to a chain length of approximately 15-10 lysine residues.

The carrier can be formed by linking a cationic moiety and a cell-specific ligand using standard cross-linking reagents which are well known in the art. The linkage is typically covalent. A preferred linkage is a peptide bond. This can be formed with a water soluble carbodiimide, such as 1-ethyl-3-(3-dimethylaminopropyl)carbodiimide hydrochloride (EDC), as described by McKee et al (1994) *Bioconjugate Chem.* 5: 306–311 or Jung, G. et al. (1981) *Biochem. Biophys. Res. Commun.* 101:599–606 or Grabarek et al. (1990) *Anal. Biochem.* 185:131. Alternative linkages are disulfide bonds which can be formed using cross-linking reagents, such as N-Succinimidyl 3-(2-pyridyldithio) propionate (SPDP), N-hydroxysuccinimidyl ester of chlorambucil, N-Succinimidyl-(4-Iodoacetyl) aminobenzoate) (SIAB), Sulfo-SIAB, and Sulfo-succinimidyl-4-maleimidophenyl-butyrate (Sulfo-SMPB). Strong noncovalent linkages, such as avidin-biotin interactions, can also be used to link cationic moieties to a variety of cell binding agents to form suitable carrier molecules.

The linkage reaction can be optimized for the particular cationic moiety and cell binding agent used to form the carrier. The optimal ratio (w:w) of cationic moiety to cell binding agent can be determined empirically. This ratio will vary with the size of the cationic moiety (e.g., polycation) being used in the carrier, and with the size of the polynucleotide to be complexed. However, this ratio generally ranges from about 0.2–5.0 (cationic moiety:ligand). Uncoupled components and aggregates can be separated from the carrier by molecular sieve or ion exchange chromatography (e.g., Aquapore™ cation exchange, Rainin).

In one embodiment of the invention, a carrier made up of a conjugate of asialoorosomucoid and polylysine is formed with the cross linking agent 1-(3-dimethylaminopropyl)-3-ethyl carbodiimide. After dialysis, the conjugate is separated from unconjugated components by preparative acid-urea polyacrylamide gel electrophoresis (pH 4–5). The conjugate can be further purified on the carboxymethyl functionalized column (see U.S. patent application Ser. No. 08/043,008, filed Apr. 5, 1993, now abandoned, the teachings of which are incorporated by reference herein).

Following formation of the carrier molecule, the polynucleotide (e.g., plasmid) is linked to the carrier so that (a) the polynucleotide is sufficiently stable (either in vivo, ex vivo, or in vitro) to prevent significant uncoupling of the polynucleotide extracellularly prior to internalization by the target cell, (b) the polynucleotide is released in functional form under appropriate conditions within the cell, (c) the polynucleotide is not damaged and (d) the carrier retains its capacity to bind to cells. Generally, the linkage between the carrier and the polynucleotide is noncovalent. Appropriate noncovalent bonds include, for example, electrostatic bonds, hydrogen bonds, hydrophobic bonds, anti-polynucleotide antibody binding, linkages mediated by intercalating agents, and streptavidin or avidin binding to polynucleotide-containing biotinylated nucleotides. However, the carrier can also be directly (e.g., covalently) linked to the polynucleotide using, for example, chemical cross-linking agents (e.g., as described in WO-A-91/04753 (Cetus Corp.), entitled "Conjugates of Antisense Oligonucleotides and Therapeutic Uses Thereof").

To form polynucleotide-carrier complexes, a solution containing carrier molecules is combined with a polynucleotide to be complexed. The solution contains a sufficient amount of a charge shielding agent to inhibit aggregation of the carrier molecules (i.e., aggregation which would occur in the absence of a charge shielding agent). In one embodiment, the carrier solution is prepared by forming carrier molecules, as described above (e.g., by conjugation of a cationic moiety and a cell binding agent), and then mixing the carrier molecules with a sufficient amount of a charge shielding agent to inhibit aggregation of the carrier molecules.

The term "charge shielding agent", as used herein, is intended to include any agent which is capable of (a) reducing charge interactions (e.g., hydrogen bonding) between individual cationic carrier molecules and/or between different parts of the same carrier molecule; and/or (b) reducing charge interactions between cationic carrier molecules and the solvent.

The term "inhibit aggregation," as used herein, refers to disaggregation and/or to prevention of aggregation of cationic carrier molecules.

The term "sufficient to inhibit aggregation of the carrier molecules," as used herein, refers to a level of disaggregation at which the carrier molecules, when complexed to polynucleotide, are easily taken up by cells and/or can easily pass through physiological barriers (e.g., blood/tissue barriers). Generally, this level of dispersity is achieved when the carrier molecules have a radius of about 20 nm or less, preferably about 15 nm or less and most preferably about 10 nm or less, as measured by laser light scattering analysis. Other methods of determining the level of aggregation of carrier molecules (alone or complexed to polynucleotide) include, for example, sucrose density gradient analysis, electron microscopy (EM), circular dichroism (CD), and spectrophotometry (e.g., absorbance at 260 nm).

In a preferred embodiment of the invention, the charge shielding agent is a salt. Suitable salts include, for example, sodium chloride (NaCl), sodium sulfate ($Na_2SO_4$), sodium phosphate ($NaH_2PO_4$), ammonium sulfate (($NH_4$)$SO_4$), ammonium phosphate ($NH_4H_2PO_4$), potassium sulfate ($K_2SO_4$), potassium phosphate ($KH_2PO_4$), potassium chloride (KCl), magnesium sulfate ($MgSO_4$), magnesium phosphate (MgHPO$_4$), magnesium chloride (MgCl$_2$), and lithium chloride (LiCl) and a variety of others. In a particularly preferred embodiment, the salt is sodium chloride (NaCl).

Other charge shielding agents which can be used to substantially disaggregate the carrier molecules include, for example, detergents and amphiphile surfactants such as the BRIJ family of polyoxyethylene fatty ethers, the SPAN sorbitan fatty acid esters, and the TWEEN polyoxyethylene derivatives of sorbitan fatty acid esters, all available from ICI Americas, Inc. of Wilmington, Del.

When using a salt (e.g., NaCl) as the charge shielding agent, the appropriate amount of salt to inhibit aggregation of the carrier molecules will vary according to the concentration of the carrier molecules. However, this concentration is generally at least about 1.0M or more. For example, for solutions containing carrier molecules at a concentration of about 0.5–20 mg/mL, the salt can be added to a concentration of about 1.0–10M. In a preferred embodiment, the carrier molecules are present in the carrier solution at a concentration of about 3.0–7.0 mg/mL, preferably about 5.0–6.0 mg/mL, and most preferably about 5.6 mg/mL. At these concentrations of carrier molecules, the carrier solutions can be prepared with salt concentrations of about 1.0–5.0M, preferably about 4.0–5.0M, and most preferably about 4.7M, respectively.

However, the appropriate amount of any given charge shielding agent to inhibit aggregation of carrier molecules can be determined empirically. For example, samples of carrier molecules can be prepared at various concentrations of a charge shielding agent as previously described, and the level of aggregation of the carrier molecules can then be examined by any of the techniques disclosed above (e.g., laser light scattering analysis, sucrose density gradient analysis, electron microscopy (EM), circular dichroism (CD), and spectrophotometry)

In addition to a charge shielding agent, the carrier solution can also optionally contain other dispersing agents to further inhibit aggregation of the carrier molecules. Aggregation of cationic carrier molecules is believed to result largely from intermolecular and intramolecular associations (e.g., hydrogen bonding) involving the net positive charge of the carrier molecules. Agents which reduce the net positive charge of the carrier molecules, therefore, can diminish these molecular associations and promote dispersity of the cationic carrier molecules.

Accordingly, in one embodiment of the invention, the carrier solution comprises a charge neutralizing agent, in addition to the charge shielding agent. The term "charge neutralizing agent", as used herein, is intended to include any agent capable of neutralizing a portion of the positive charge of cationic carrier molecules (i.e., by deprotonation). In a preferred embodiment of the invention, the charge neutralizing agent is a base. Suitable bases include, for example, sodium hydroxide (NaOH), potassium hydroxide (KOH), ammonium hydroxide (NH$_4$OH), alkylamines, alkoxides and triethanolamines. In a particularly preferred embodiment, the base is sodium hydroxide.

The cationic carrier solution contains the charge neutralizing agent in an amount sufficient to neutralize a portion of the positive charge of the carrier molecules. This partial neutralization reduces charge associations and aggregation of the carrier molecules, while still maintaining an overall net positive charge associated with the carrier molecules (so that they are able to electrostatically bind negatively charged polynucleotides). In one embodiment of the invention, the charge neutralizing agent is added to the carrier solution in an amount sufficient to neutralize about 5 to 20% (e.g., about 10%) of the positive charge of the carrier molecules. The charge neutralizing agent may be added to the carrier solution before, after or concurrently with the charge shielding agent.

When using a base as the charge neutralizing agent, the carrier solution can be prepared with a concentration of base (e.g., NaOH) of about 10–1000 mM, preferably about 10–100 mM, more preferably about 50–70 mM, and most preferably about 59 mM, for carrier solutions containing carrier molecules at a concentration of about 0.5–20 mg/mL, preferably about 3–7 mg/mL, more preferably about 5–6 mg/mL, and most preferably about 5.6 mg/mL, respectively. The carrier solution can then be mixed vigorously to promote disaggregation of molecular carrier aggregates.

The polynucleotide to be complexed is combined (and allowed to equilibrate) with the carrier solution to form substantially disperse and soluble polynucleotide-carrier complexes. The polynucleotide is combined with the carrier solution so that the polynucleotide-carrier solution contains a final concentration of charge shielding agent and, optionally, charge neutralizing agent which does not damage or induce any substantial conformational change (e.g., denature) in the polynucleotide so that it remains substantially functional and in a form suitable for complexing with the carrier molecules. Generally, this corresponds to a final concentration of charge shielding agent (e.g., salt) of less than 1.0M, preferably less than 0.75M, and most preferably less than 0.5M (e.g., about 0.15–0.5M), and a concentration of charge neutralizing agent of less than 10 mM, preferably less than 4.0 mM, and most preferably about 2.0 mM.

In one embodiment, the polynucleotide is diluted, for example, with nanopure water, prior to (or concurrently with) being combined with a carrier solution to a concentration which, when combined with the carrier solution, results in the desired final concentration of charge shielding agent (e.g., salt) and charge neutralizing agent (e.g., base). When adding the polynucleotide to a carrier solution containing a salt (e.g., NaCl) as the charge shielding agent, the polynucleotide can be diluted to a concentration which results in a final salt concentration (i.e., after mixing with carrier solution) of less than 1.0M, preferably less than 0.5M, more preferably about 0.15–0.5M and most preferably about 0.3M (about two times physiological). At this concentration of salt, the carrier molecules maintain a high level of dispersity and the polynucleotide remains functional.

If the carrier solution contains a charge neutralizing agent (e.g., a base), along with the charge shielding agent, then the final concentration of charge neutralizing agent in the carrier solution, following addition of the polynucleotide, should also be a concentration which does not substantially damage, alter, or inhibit the function of the polynucleotide. For example, when using a base as the charge neutralizing agent, the polynucleotide-carrier solution can contain a final base concentration of less than 50 mM, preferably less than 10 mM, more preferably less than 4.0 mM (e.g., about 1.0–4.0 mM), and most preferably about 2.0 mM.

In a preferred embodiment of the invention, the final solution in which the polynucleotide-carrier complexes are formed has (a) a carrier molecule concentration of about 3.0–7.0 mg/mL, preferably about 5.0–6.0 mg/mL, (b) a salt concentration of about 0.15–0.5M, preferably about 0.3M, (c) a base concentration of about 1.0–4.0 mM, preferably about 2.0 mM and (c) an appropriate final concentration of DNA (e.g., 10 µg/mL).

The polynucleotide is combined with the carrier solution in an amount appropriate to form stable complexes which remain soluble in solution. Generally, the polynucleotide is added to the carrier solution in a weight to weight (w:w) ratio (polynucleotide to carrier) of about 1:0.2–1:20, (e.g., about 1:1–1:10, or about 1:1.5–1:5). Complexes formed with these weight ratios (polynucleotide to carrier) have corresponding charge neutralization ratios (i.e., percent neutralization of negatively charge polynucleotide by positively charged carrier) of about 10–1000% (e.g., about 50–500%, or about 75–250%), respectively.

The performance of a given polynucleotide-carrier complex can be affected by the level of polynucleotide charge neutralization in the complex. The optimal level of polynucleotide charge neutralization for a given complex can depend on a variety of factors, including the nature of the polynucleotide (e.g., plasmid DNA) and the size and charge of the particular cationic carrier molecule used. While appropriate levels of polynucleotide charge neutralization for complexes generally fall within the ranges provided above, the optimal level for a given complex can be determined empirically. For example, a series of preparations can be made for a particular complex each with varying degrees of polynucleotide charge neutralization. The performance of these samples can then be tested by, for example, measuring levels of expression obtained with each sample either in vitro or in in vivo expression assays.

Additional steps also can be taken which further diminish aggregation of complexes, as well as reduce the size of the complexes and increase their homogeneity, thereby improving their performance (e.g., level of gene expression). Such measures include, for example, extrusion of the complexes, temperature variations, pH changes and measures which diminish inhibitory actions which occur in vivo (e.g., opsonization of the complex by inhibitory factors present in blood serum).

Accordingly, in another embodiment of the invention, the polynucleotide-carrier complexes are extruded through an appropriate filter after being formed but prior to being administered to cells (either in vitro or in vivo). The term "extrusion" or "extruded", as used herein, means passage of the complexes through a filtering apparatus, followed by collection of the filtered product. Extrusion of complexes significantly (1) decreases the size of the complexes (2) increases the homogeneity of the complexes, and (3) improves the performance of the complexes, as measured by gene expression levels. While any extrusion apparatus which diminishes larger complexes and increases the proportion of smaller, more homogenous complexes may be used, a preferred apparatus for extruding complexes is a 50 nm filter attached to an Emulsi-Flex-C5 (Avestin, Inc. Ottawa, Canada).

Compositions of polynucleotide-carrier complexes, formed as described herein, can be used either in vitro or in vivo for cellular targeting of expression vectors (e.g., plasmids) containing intronless genes having one or more near-consensus splice sequences operably linked to one or more viral PRE sequences.

For in vitro delivery of expression vectors of the invention, cultured cells can be incubated with the polynucleotide-carrier complexes in an appropriate medium under conditions conducive to endocytotic uptake by the cells.

For in vivo delivery of expression vectors of the invention to cells, the polynucleotide-carrier complexes can be administered to a subject in a pharmaceutically acceptable vehicle.

The term "pharmaceutically acceptable carrier", as used herein, is intended to include any physiologically acceptable carrier for stabilizing polynucleotide-carrier complexes of the present invention for administration in vivo, including, for example, saline and aqueous buffer solutions, solvents, dispersion media, antibacterial and antifungal agents, isotonic and absorption delaying agents, and the like. The use of such media and agents for pharmaceutically active substances is well known in the art. Except insofar as any conventional media is incompatible with the polynucleotide-carrier complexes of the present invention, use thereof in a therapeutic composition is contemplated.

In all cases, the pharmaceutical composition must be sterile and must be fluid to the extent that easy syringability exists. It must be stable under the conditions of manufacture and storage and must be preserved against the contaminating action or microorganisms such as bacteria and fungi. Protection of the polynucleotide-carrier complexes from degradative enzymes (e.g., nucleases) can be achieved by including in the composition a protective coating or nuclease inhibitor. Prevention of the action of microorganisms can be achieved by various anti-bacterial and anti-fungal agents, for example, parabens, chlorobutanol, phenol, ascorbic acid, thimerosal, and the like.

Polynucleotide-carrier complexes of the invention may be administered in vivo by any suitable route of administration. The appropriate dosage may vary according to the selected route of administration. The complexes are preferably injected intravenously in solution containing a pharmaceutically acceptable carrier, as defined herein. Sterile injectable solutions can be prepared by incorporating the polynucleotide-carrier complexes in the required amount in an appropriate buffer with one or a combination of ingredients enumerated above, as required, followed by filtered sterilization. Other suitable routes of administration include intravascular, subcutaneous (including slow-release implants), topical and oral.

Appropriate dosages may be determined empirically, as is routinely practiced in the art. Mice can be administered dosages of up to 1.0 mg of polynucleotide per 20 g of mouse, or about 1.0 mL of complex per 1.4 mL of mouse blood.

This invention is illustrated further by the following examples which should not be construed as further limiting the subject invention. The contents of all references and published patent applications cited throughout this application are hereby incorporated by reference.

EXAMPLE 1

Preparation of Expression Plasmids Containing Factor VIII cDNA and the HBV PRE Sequence An expression vector containing the post-transcriptional regulatory element (PRE) of HBV inserted downstream of the translation stop codon of Factor VIII B-domain deleted cDNA was prepared as follows:

The PRE sequence was excised as a 587 base pair stu-1 restriction fragment (SEQ ID NO: 1) from a plasmid, pADW-HTD HBV, containing two head-to-tail copies of the hepatitis B virus (HBV) genome. The fragment, corresponding to bases 1118 to 1704 of pADW-HTD, was then cloned into the pcDNA1 expression vector (InVitrogen, Inc.) along with Factor VIII B-domain deleted cDNA. The fragment was inserted at a position 3' of the Factor VIII stop codon and 5' of the polyadenylation signal.

The entire 9354 base pair sequence of the resulting plasmid, pCDNAF8ΔK+PRE, is provided in SEQ ID NO: 2.

The coding region of the Factor VIII cDNA sequence extends from bases 2965 to 7377 of SEQ ID NO: 2. The 587 base pair PRE fragment extends from bases 7611 to 8197 of SEQ ID NO: 2.

Figure 7:
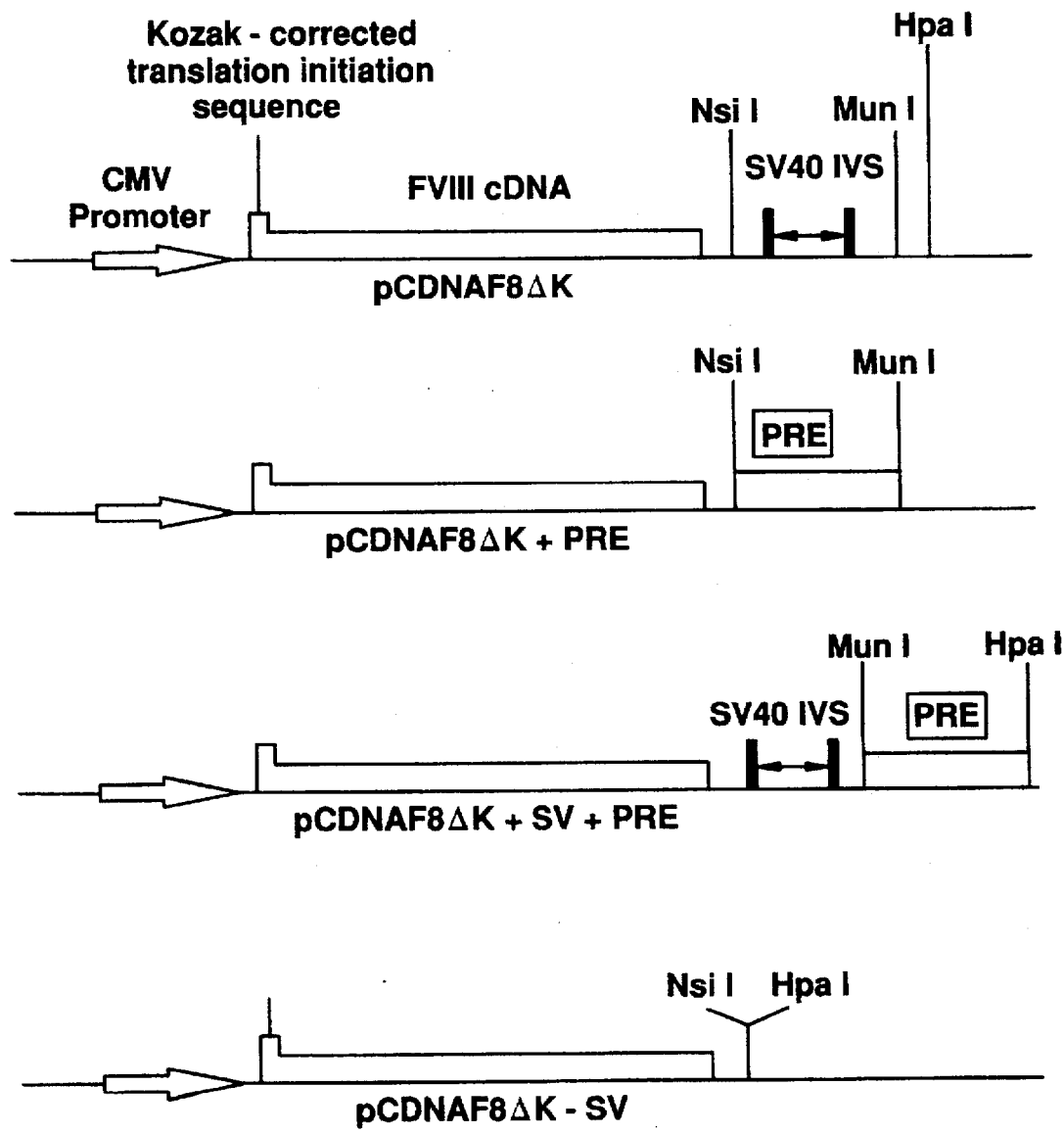
FIG. 7 shows a map of four expression vector constructs containing cDNA encoding B-domain deleted Factor VIII with and without the HBV PRE sequence (SEQ ID NO: 1) and the 3' SV40 IVS.

For purposes of comparison, the same expression vector was constructed (a) with the SV40 intervening sequence (IVS) at a position 3' of the stop codon and 5' of the PRE and polyadenylation signal (pCDNAF8ΔK+SV+PRE); and (b) without the PRE fragment but with the SV40 IVS (pCDNAF8ΔK-SV). A map of these expression vectors is shown in FIG. 7.

EXAMPLE 2

In Vitro Expression of Plasmids Containing Factor VIII cDNA and HBV PRE

Figure 8:
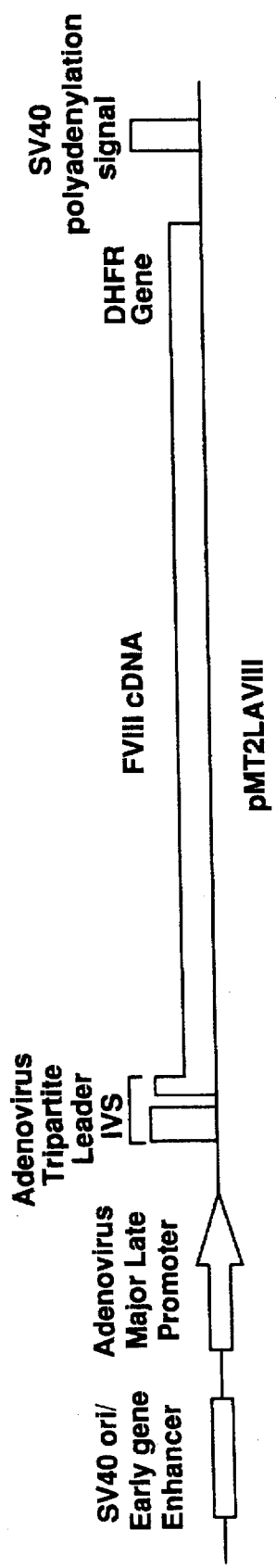
FIG. 8 shows a map of an expression vector, pMT2LA VIII, containing cDNA encoding B-domain deleted Factor VIII with and a 3' IVS.

To study the effect on cytoplasmic accumulation and expression of Factor VIII mRNA caused by the presence of the HBV PRE sequence and the SV40 IVS, each of the vectors prepared in Example 1 was transfected at a concentration of 2.5 μg/ml into HuH-7 human carcinoma cells using the calcium phosphate precipitation method described by O'Mahoney et al. (1994) *DNA & Cell Biol.* 13(12): 1227–1232. An expression plasmid, pMT2LA8 (Pitman et al. (1993) *Blood* 81(11):2925–2935), containing Factor VIII B-domain deleted cDNA, was also transfected into cells. A map of pMT2LA8 is shown in FIG. 8.

Cells were also co-transfected with 2.5 ng/ml of an expression plasmid encoding human Growth Hormone (pCMVHGH) to normalize transfection levels.

Figure 2A:
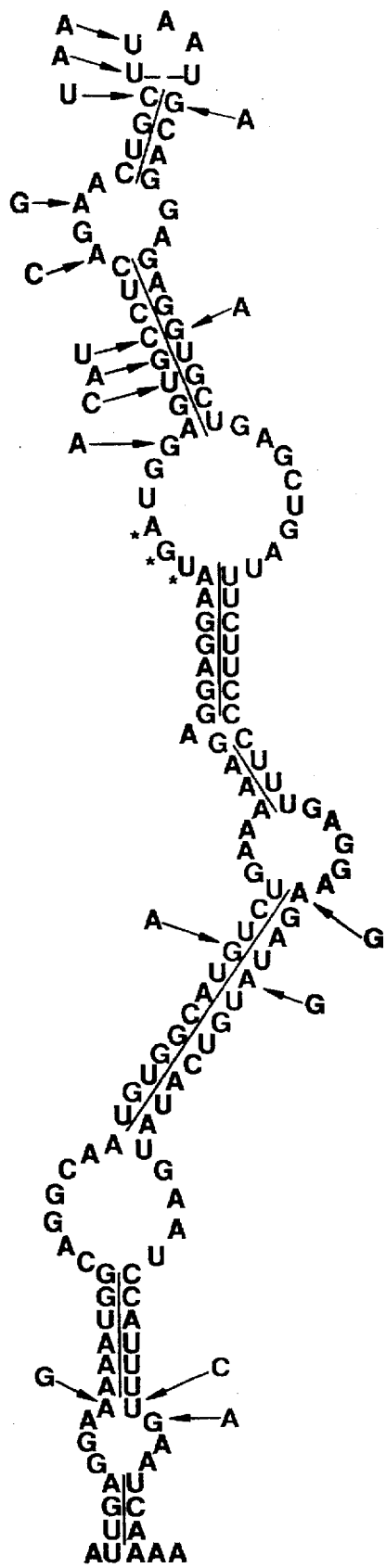
FIG. 2 shows the calculated secondary RNA structure of the Rev-Response Element (RRE) (SEQ ID NO: 18) of feline immunodeficiency virus (FIV) and the Post-Transcriptional Regulatory Element (PRE) of hepatitis B virus.
Figure 2B:
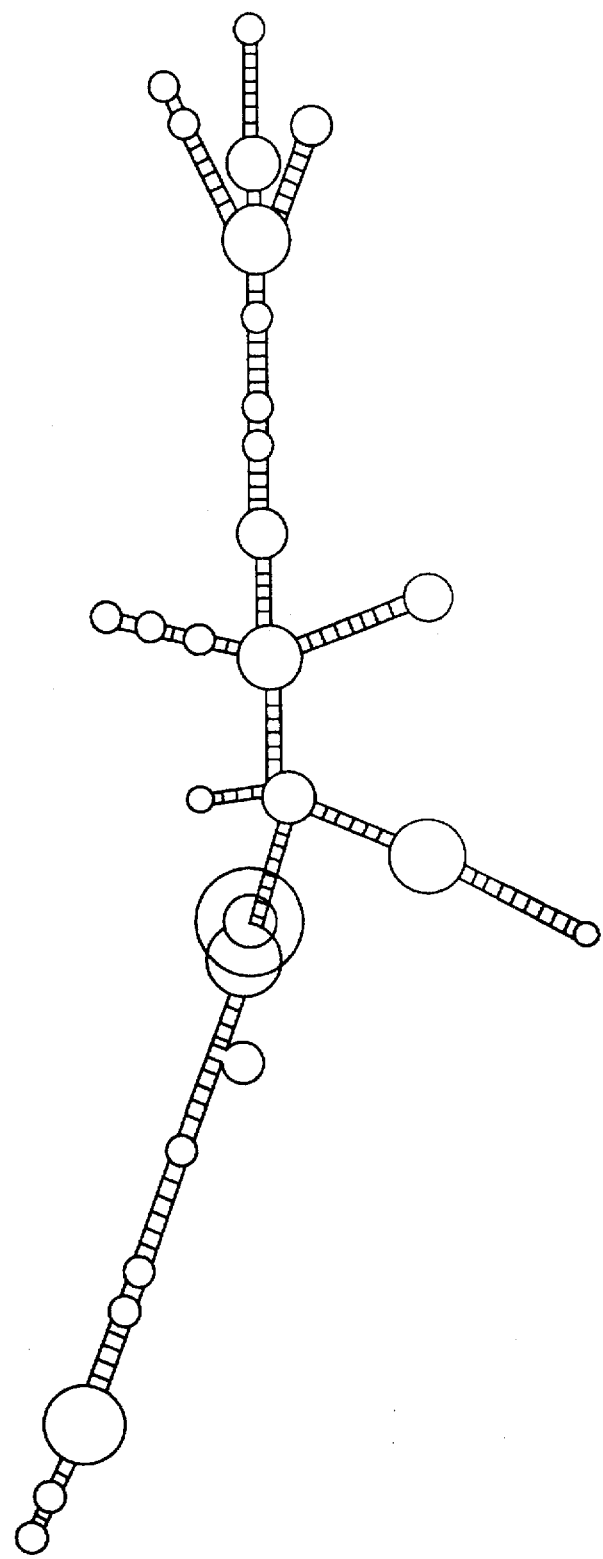
Figure 3:
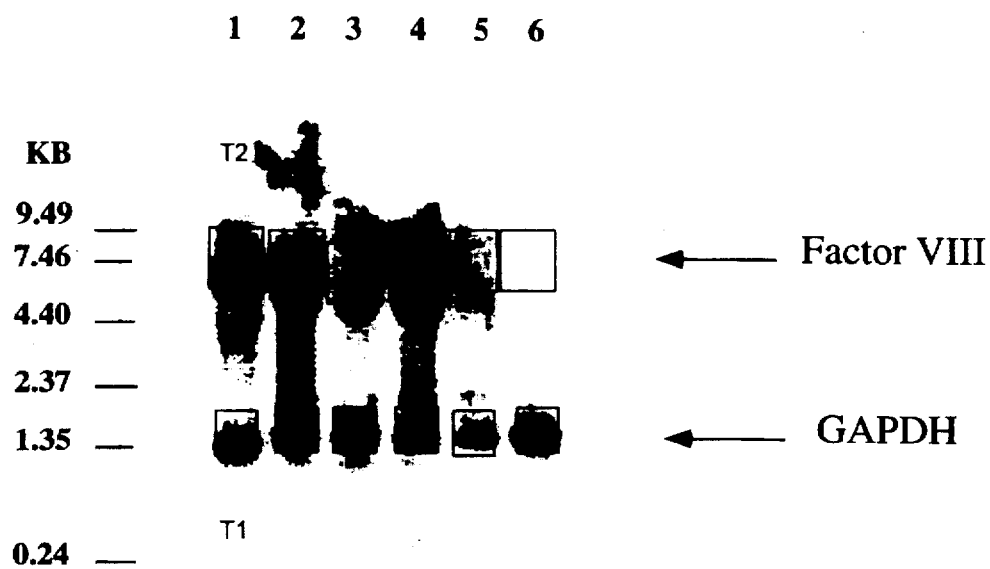
FIG. 3 shows a Northern Blot analysis comparing human B-domain deleted Factor VIII RNA levels in HUH-7 cells transfected with plasmids containing cDNA encoding B-domain deleted Factor VIII with and without the 3' SV40 intervening sequence (IVS) and the HBV PRE sequence (SEQ ID NO: 1).

To measure mRNA levels, Northern blot analysis was performed on cells 24 hours post-transfection. Levels of Factor VIII mRNA were measured by standard techniques (i.e., as described by Sambrook et al. "Molecular Cloning" 2d ed.) and normalized to glyceraldehyde phosphate dehydrogenase (GAPDH) RNA. As shown in FIG. 3, the presence of the PRE sequence without the SV40 IVS sequence caused a greater than 2–5 fold increase in the amount of normalized Factor VIII mRNA (see lane 4 of FIG. 3) compared to expression plasmids not containing the PRE sequence (see lanes 1–3).

To measure Factor VIII expression levels, protein assays were performed 48 hours post transfection by quantitative ELISA (Zatloukal et al. (1994) *PNAS* 91: 5148–5152), and by an activity assay (KabiCoATest, purchased from Kabi Inc., Sweden). HGH protein levels were measured by radioimmunoassay (RIA) (Nichol's Institute). The results are shown in FIGS. 4 and 5.

Figure 4A:
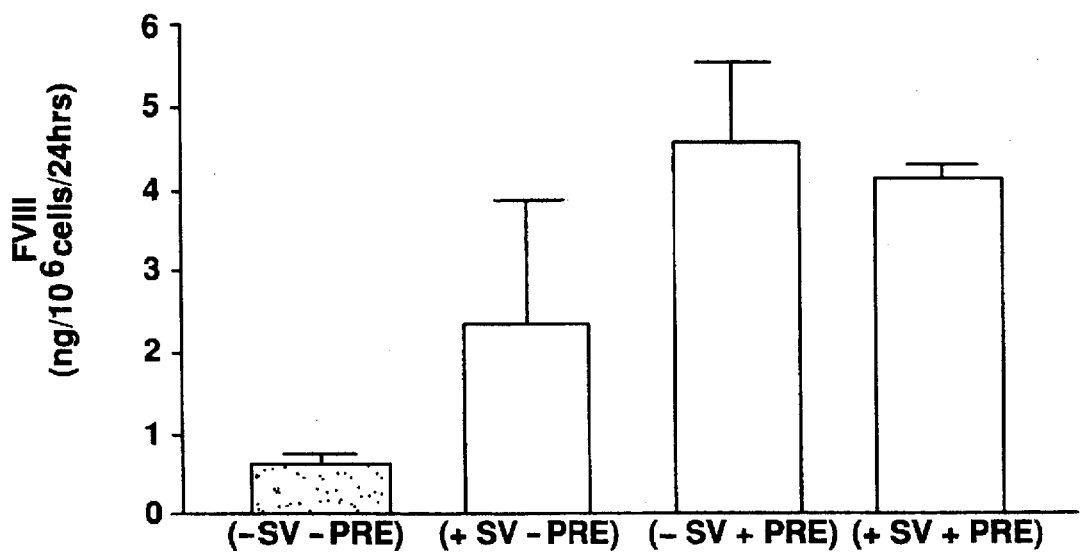
FIG. 4 is a graphic representation showing the effect on expression of human B-domain deleted Factor VIII caused by the presence of the HBV PRE sequence (SEQ ID NO: 1) and the 3' SV40 IVS in Factor VIII expression vectors. Protein levels were measured both by ELISA and by activity.
Figure 4B:
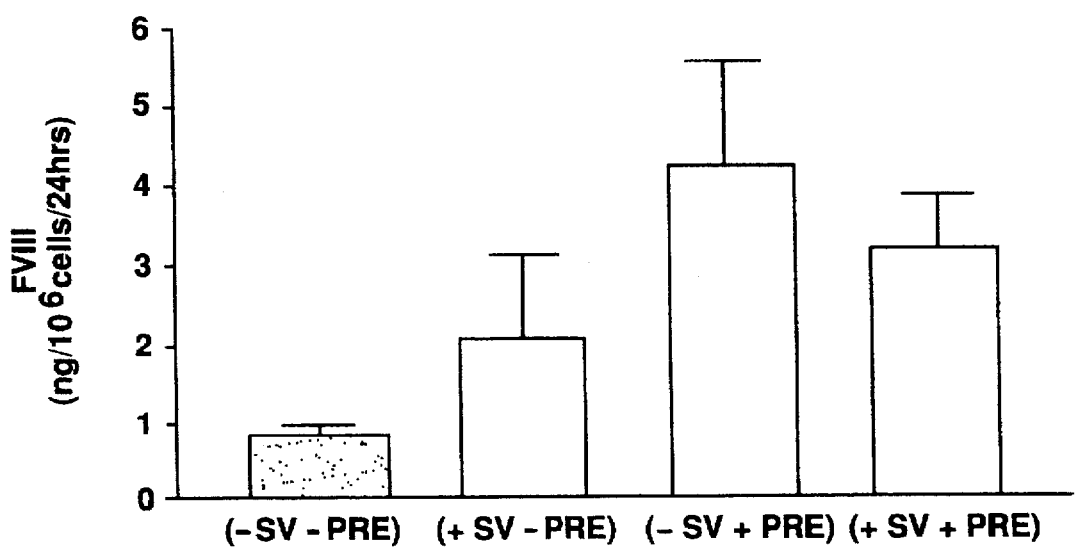

As shown in FIG. 4, both the activity (KabiCoATest) and the amount of Factor VIII protein expressed (measured by ELISA) was greatest in cells transfected with plasmids containing the HBV PRE sequence (−SV+PRE and +SV+PRE).

Figure 5:
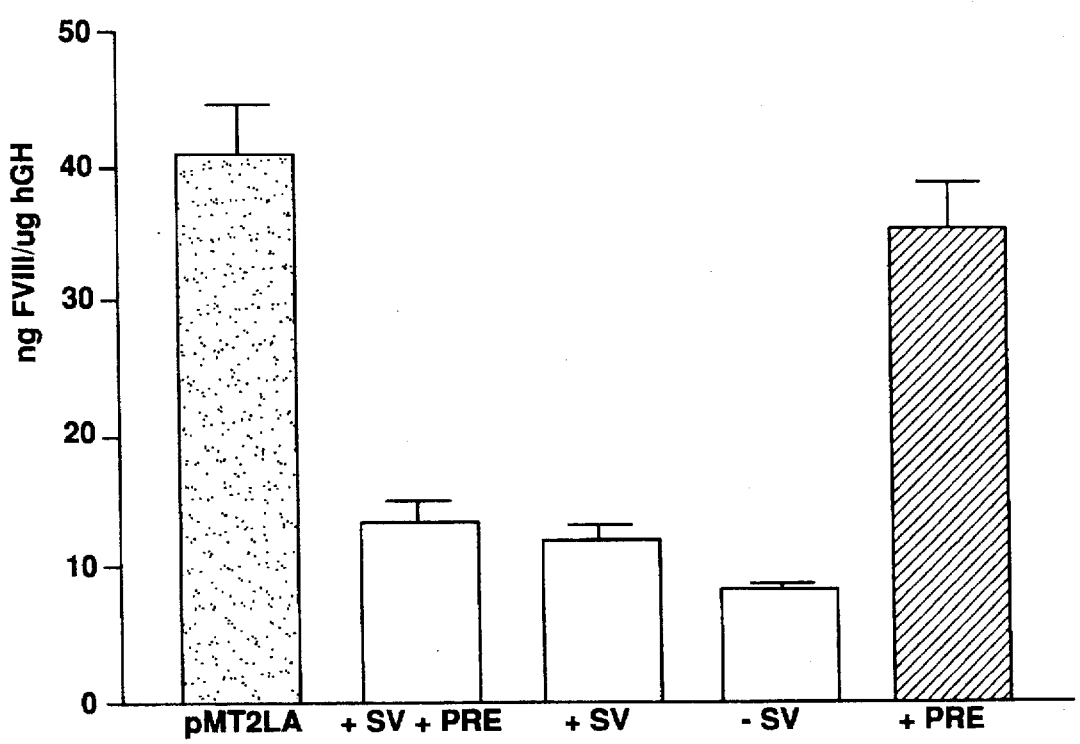
FIG. 5 is a graphic representation showing the effect on human B-domain deleted Factor VIII expression, normalized to human Growth Hormone expression, of the HBV PRE sequence (SEQ ID NO: 1) and the 3' SV40 intervening sequence (IVS) in expression vectors. Protein levels were measured by radioimmunoassay.

FIG. 5 shows the results of Factor VIII expression (measured by ELISA) in transfection normalized cells (i.e., cells co-transfected with plasmid encoding HGH and measured by RIA). Again, the presence of the PRE sequence (plasmid pcF8ΔK+PRE) caused an up to 5-fold increase in Factor VIII expression compared to plasmids not containing the PRE sequence. Interestingly, the highest level of Factor VIII expression was obtained from pMT2LA, with plasmid pcF8ΔK+PRE being slightly lower. However, the reverse was true for the amount of RNA present in the cells which was greatest for pcF8ΔK+PRE and lower for pMT2LA, as measured by Northern Blot analysis (FIG. 3).

This suggests that not all of the Factor VIII transcripts from pcF8ΔK+PRE are being translated into protein and that additional genetic regulatory elements are needed in the plasmid, most likely in the 5' region since this region differs in pMT2LA and pcF8ΔK+PRE, to optimize expression levels. Such additional elements may include tissue-specific enhancers, alternate promoter and leader sequences, or additional copies of the PRE sequence.

EXAMPLE 3

In Vivo Targeted Expression of an Expression Plasmid Containing Factor VIII cDNA and the HBV PRE For in vivo expression studies, a plasmid (pMT$_2$F8PREIVSpAGH-E/O) containing Factor VIII B-domain deleted cDNA and elements (e.g., EBNA-1 and Ori P) from the pCEP4 vector (InVitrogen Inc.) was prepared. The PRE sequence was located 3' of the Factor VIII stop codon and 5' of human Growth Hormone gene polyadenylation signal so that it would be transcribed but not translated.

The plasmid was then targeted for delivery to liver as follows:

I. Formation of targeted complexes containing pMT$_2$F8PREIVSpAGH-E/O

Conjugates of ASOR and poly-L-lysine were prepared by carbodiimide coupling similar to that reported by McKee et al (1994) *Bioconjugate Chem.* 5: 306–311. In brief, ASOR, 26 kD poly-L-lysine and EDC in a 1:1:0.5 mass ratio were reacted as follows. EDC (dry) was added directly to a stirring aqueous ASOR solution. 26 kD Polylysine was added and the reaction mixture was adjusted to pH 5.5–6.0 and stirred for two hours at ambient temperature. ASOR concentration was 5 mg/mL in the final reaction conditions. The reaction was quenched by addition of Na$_3$PO$_4$ (200 mM, pH 11) to a final concentration of 10 mM. The conjugate was first purified on a Fast Flow Q Sepharose anion exchange chromatography column (Pharmacia) eluted with 50 mM Tris, pH 7.5, and then dialyzed against ultra-pure water.

The ASOR-poly-L-lysine conjugate, at a concentration of about 5.6 mg/mL, was aliquoted into a reaction vessel to which was added an amount of 5M NaCl to obtain a final concentration of about 4.7M NaCl and an amount of 1M NaOH to obtain a final concentration of about 59 mM NaOH. The solutions were mixed vigorously.

The Factor VIII/PRE plasmid in 10 mM Tris-HCl, 1 mM EDTA buffer was diluted by adding nanopure water and then combined with the carrier solution to achieve a final concentration of 300 mM NaCl and 2 mM NaOH.

Complexes were formed with a ratio of DNA to carrier sufficient to neutralize 50% of the negative charge of the DNA. To determine this ratio, an aliquot of the purified dialyzed conjugate solution was lyophilized, weighed and dissolved in ultra-pure water at a specific concentration (w/v). Since polylysine has minimal absorbance at 280 nm, the ASOR component of the conjugate (w/v) was calculated using the extinction co-efficient at 280 nm. The composition of the conjugate was estimated by comparison of the concentration of the conjugate (w/v) with the concentration of ASOR (w/v) as determined by UV absorbance. The difference between the two determinations was attributed to the polylysine component of the conjugate. The ratio of conjugate to DNA (w:w) necessary for charge neutralization was then calculated using the determined cationic composition.

The materials and methods used in the protocols described above are as follows: Protamine, Poly-L-lysine (26 kD; mean MW) was purchased from Sigma Chemical Co., St. Louis, Mo. 1-[3-(dimethylamino)-propyl]-3-ethylcarbodiimide (EDC) was purchased from Aldrich Chemical Co, Milwaukee, Wis. Orosomucoid was purchased from Alpha Therapeutics, Los Angeles, Calif. Asialoorosomucoid (ASOR) was prepared from Orosomucoid (15 mg/ml) by hydrolysis with 0.1N sulfuric acid at 76° C. for one hour. ASOR was purified from the reaction mixture by neutralization with 1.0N NaOH to pH 5.5 and exhaustive dialysis against water at room temperature. ASOR concentration was determined using an extinction coefficient of 0.92 mL mg$^{-1}$, cm$^{-1}$ at 280 nm. The thiobarbituric acid assay of Warren (1959) *J. Biol Chem.* 234: 1971–1975 was used to verify desialylation of the OR. ASOR prepared by the above method was determined to be 98% desialylated.

II. Expression Assays Using Targeted pMT$_2$F8PREIVSpAGH-E/O

Figure 6:
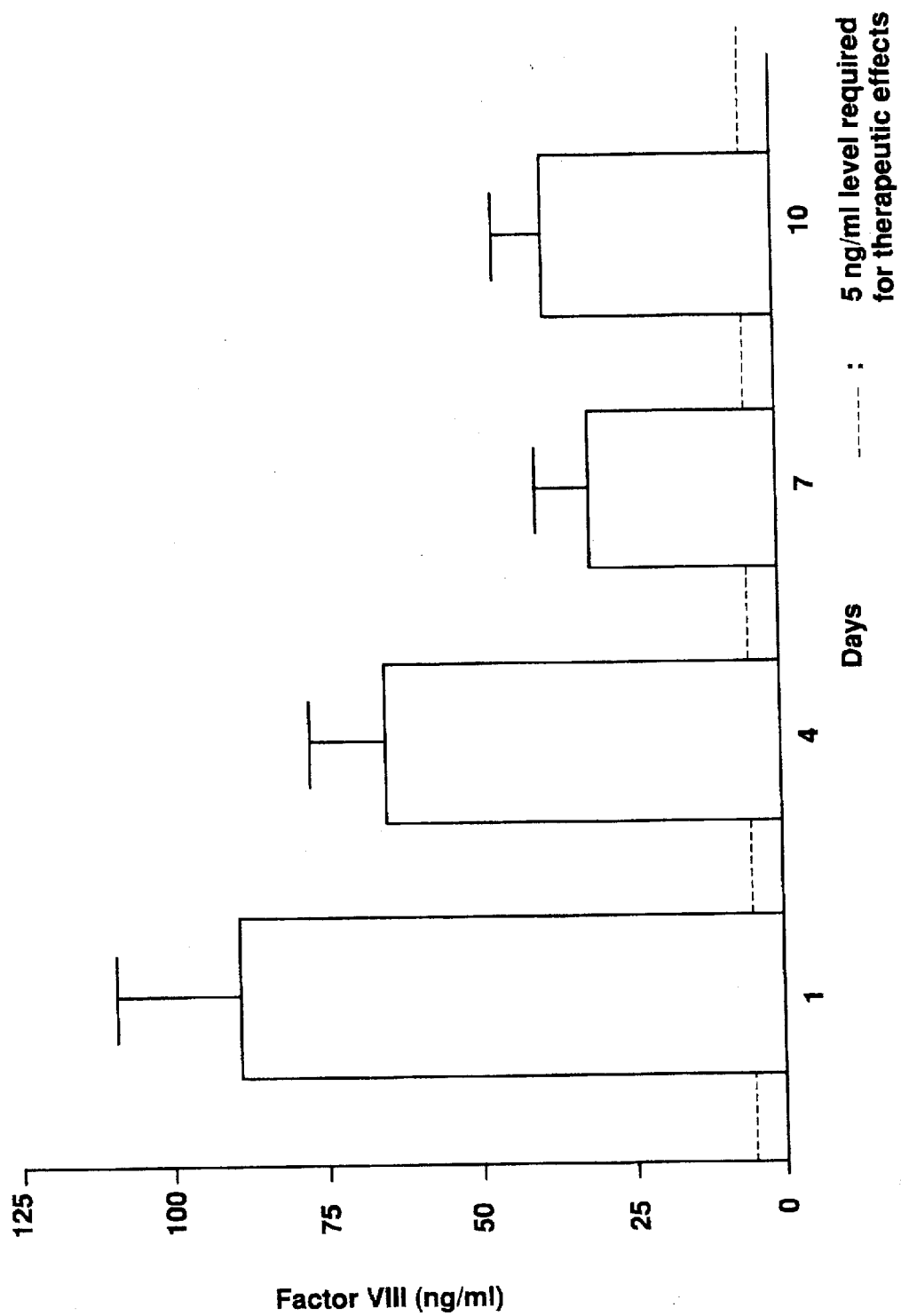
FIG. 6 is a graphic representation showing in vivo levels of human B-domain deleted Factor VIII expression in mice at 1, 4, 7 and 10 days following injection with a targeted complex containing a plasmid, pMT$_2$F8PREIVSpAGH-E/O, encoding human B-domain deleted Factor VIII and including both the HBV PRE sequence (SEQ ID NO: 1) and a 3' IVS sequence.

Five mice were injected via tail vein with 1.0 ml of pMTF8 PRE IVS GHpA E/O plasmid complex (10 µg total DNA/mouse). Mice were sacrificed 1, 4, 7 and 10 days post injection and their livers removed and assayed for Factor VIII by ELISA. The results are shown in FIG. 6 and demonstrate that significant Factor VIII expression was obtained out to 10 days. While 5 ng/ml of blood is required for therapeutic effects, the average levels of Factor VIII measured at days 1, 4, 7 and 10 were 82.4, 72.3, 47.5 and 50.2 ng/ml of blood, respectively.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A vector comprising (a) an intronless gene containing one or more near consensus splice sequences operably linked to a promoter sequence so that the gene is transcribed in a cell, and (b) one or more copies of a viral cis-acting post-transcriptional regulatory element which is transcribed along with the gene and causes export of the gene transcript from the nucleus into the cytoplasm of the cell.

2. The vector of claim 1 wherein the gene is a cDNA.

3. The vector of claim 1 wherein the viral cis-acting post-transcriptional regulatory element is derived from hepatitis B virus.

4. The vector of claim 3 wherein the viral cis-acting post-transcriptional regulatory element comprises the nucleotide sequence of SEQ ID NO: 1.

5. The vector of claim 4, comprising two or more copies of a viral cis-acting post-transcriptional regulatory element.

6. The vector of claim 1 wherein the gene encodes a blood coagulation factor.

7. The vector of claim 6 wherein the gene encodes Factor VIII.

8. The vector of claim 6 wherein the gene encodes Factor IX.

9. A method for increasing expression of an intronless gene containing one or more near consensus splice sites, the method comprising operably linking one or more copies of a viral cis-acting post-transcriptional regulatory element to the gene so that the post-transcriptional regulatory element is transcribed along with the gene as a gene transcript and causes export of the gene transcript from the nucleus into the cytoplasm of a cell.

10. The method of claim 9 wherein the gene is a cDNA.

11. The method of claim 9 wherein the viral cis-acting post-transcriptional regulatory element is derived from hepatitis B virus.

12. The method of claim 11 wherein the viral cis-acting post-transcriptional regulatory element comprises the nucleotide sequence of SEQ ID NO: 1.

13. The method of claim 9 wherein the gene encodes a blood coagulation factor.

14. The method of claim 13 wherein the blood coagulation factor is Factor VIII.

15. The method of claim 13 wherein the blood coagulation factor is Factor IX.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
    ( A ) LENGTH: 587 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:1:

```
CCTTTCTAAG  TAAACAGTAC  ATGAACCTTT  ACCCGTTGC   TCGGCAACGG  CCTGGTCTGT       60

GCCAAGTGTT  TGCTGACGCA  ACCCCACTG   GCTGGGGCTT  GGCCATAGGC  CATCAGCGCA      120

TGCGTGGAAC  CTTTGTGGCT  CCTCTGCCGA  TCCATACTGC  GGAACTCCTA  GCCGCTTGTT      180

TTGCTCGCAG  CCGGTCTGGA  GCAAAGCTCA  TCGGAACTGA  CAATTCTGTC  GTCCTCTCGC      240

GGAAATATAC  ATCGTTTCCA  TGGCTGCTAG  GCTGTACTGC  CAACTGGATC  CTTCGCGGGA      300

CGTCCTTTGT  TTACGTCCCG  TCGGCGCTGA  ATCCGCGGA   CGACCCCTCT  CGGGGCCGCT      360

TGGGACTCTC  TCGTCCCCTT  CTCCGTCTGC  CGTTCCAGCC  GACCACGGGG  CGCACCTCTC      420

TTTACGCGGT  CTCCCCGTCT  GTGCCTTCTC  ATCTGCCGGT  CCGTGTGCAC  TTCGCTTCAC      480

CTCTGCACGT  TGCATGGAGA  CCACCGTGAA  CGCCCATCAG  ATCCTGCCCA  AGGTCTTACA      540

TAAGAGGACT  CTTGGACTCC  CAGCAATGTC  AACGACCGAC  CTTGAGG                    587
```

( 2 ) INFORMATION FOR SEQ ID NO:2:

( i ) SEQUENCE CHARACTERISTICS:
    ( A ) LENGTH: 9354 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 2965..7378

( x i ) SEQUENCE DESCRIPTION: SEQ ID NO:2:

```
GGCGTAATCT GCTGCTTGCA AACAAAAAAA CCACCGCTAC CAGCGGTGGT TTGTTTGCCG        60
GATCAAGAGC TACCAACTCT TTTTCCGAAG GTAACTGGCT TCAGCAGAGC GCAGATACCA       120
AATACTGTCC TTCTAGTGTA GCCGTAGTTA GGCCACCACT TCAAGAACTC TGTAGCACCG       180
CCTACATACC TCGCTCTGCT AATCCTGTTA CCAGTGGCTG CTGCCAGTGG CGATAAGTCG       240
TGTCTTACCG GGTTGGACTC AAGACGATAG TTACCGGATA AGGCGCAGCG GTCGGGCTGA       300
ACGGGGGGTT CGTGCACACA GCCCAGCTTG GAGCGAACGA CCTACACCGA ACTGAGATAC       360
CTACAGCGTG AGCATTGAGA AAGCGCCACG CTTCCCGAAG GGAGAAAGGC GGACAGGTAT       420
CCGGTAAGCG GCAGGGTCGG AACAGGAGAG CGCACGAGGG AGCTTCCAGG GGGAAACGCC       480
TGGTATCTTT ATAGTCCTGT CGGGTTTCGC CACCTCTGAC TTGAGCGTCG ATTTTTGTGA       540
TGCTCGTCAG GGGGGCGGAG CCTATGGAAA AACGCCAGCA ACGCAAGCTA GCTTCTAGCT       600
AGAAATTGTA AACGTTAATA TTTTGTTAAA ATTCGCGTTA AATTTTTGTT AAATCAGCTC       660
ATTTTTTAAC CAATAGGCCG AAATCGGCAA AATCCCTTAT AAATCAAAAG AATAGCCCGA       720
GATAGGGTTG AGTGTTGTTC CAGTTTGGAA CAAGAGTCCA CTATTAAAGA ACGTGGACTC       780
CAACGTCAAA GGGCGAAAAA CCGTCTATCA GGGCGATGGC CGCCCACTAC GTGAACCATC       840
ACCCAAATCA AGTTTTTTGG GGTCGAGGTG CCGTAAAGCA CTAAATCGGA ACCCTAAAGG       900
GAGCCCCCGA TTTAGAGCTT GACGGGGAAA GCCGGCGAAC GTGGCGAGAA AGGAAGGGAA       960
GAAAGCGAAA GGAGCGGGCG CTAGGGCGCT GGCAAGTGTA GCGGTCACGC TGCGCGTAAC      1020
CACCACACCC GCCGCGCTTA ATGCGCCGCT ACAGGGCGCG TACTATGGTT GCTTTGACGA      1080
GACCGTATAA CGTGCTTTCC TCGTTGGAAT CAGAGCGGGA GCTAAACAGG AGGCCGATTA      1140
AAGGGATTTT AGACAGGAAC GGTACGCCAG CTGGATTACC AAAGGGCCTC GTGATACGCC      1200
TATTTTTATA GGTTAATGTC ATGATAATAA TGGTTTCTTA GACGTCAGGT GGCACTTTTC      1260
GGGGAAATGT GCGCGGAACC CCTATTTGTT TATTTTTCTA AATACATTCA AATATGTATC      1320
CGCTCATGAG ACAATAACCC TGATAAATGC TTCAATAATA TTGAAAAAGG AAGAGTATGA      1380
GTATTCAACA TTTCCGTGTC GCCCTTATTC CCTTTTTTGC GGCATTTTGC CTTCCTGTTT      1440
TTGCTCACCC AGAAACGCTG GTGAAAGTAA AAGATGCTGA AGATCAGTTG GGTGCACGAG      1500
TGGGTTACAT CGAACTGGAT CTCAACAGCG GTAAGATCCT TGAGAGTTTT CGCCCCGAAG      1560
AACGTTTTCC AATGATGAGC ACTTTTAAAG TTCTGCTATG TGGCGCGGTA TTATCCCGTG      1620
TTGACGCCGG GCAAGAGCAA CTCGGTCGCC GCATACACTA TTCTCAGAAT GACTTGGTTG      1680
AGTACTCACC AGTCACAGAA AAGCATCTTA CGGATGGCAT GACAGTAAGA GAATTATGCA      1740
GTGCTGCCAT AACCATGAGT GATAACACTG CGGCCAACTT ACTTCTGACA ACGATCGGAG      1800
GACCGAAGGA GCTAACCGCT TTTTGCACA ACATGGGGGA TCATGTAACT CGCCTTGATC      1860
GTTGGGAACC GGAGCTGAAT GAAGCCATAC CAAACGACGA GCGTGACACC ACGATGCCTG      1920
CAGCAATGGC AACAACGTTG CGCAAACTAT TAACTGGCGA ACTACTTACT CTAGCTTCCC      1980
GGCAACAATT AATAGACTGG ATGGAGGCGG ATAAAGTTGC AGGACCACTT CTGCGCTCGG      2040
CCCTTCCGGC TGGCTGGTTT ATTGCTGATA AATCTGGAGC CGGTGAGCGT GGGTCTCGCG      2100
GTATCATTGC AGCACTGGGG CCAGATGGTA AGCCCTCCCG TATCGTAGTT ATCTACACGA      2160
CGGGGAGTCA GGCAACTATG GATGAACGAA ATAGACAGAT CGCTGAGATA GGTGCCTCAC      2220
TGATTAAGCA TTGGTAACTG TCAGACCAAG TTTACTCATA TATACTTTAG ATTGATTTAA      2280
AACTTCATTT TTAATTTCTC TAGCGCGTTG ACATTGATTA TTGACTAGTT ATTAATAGTA      2340
```

-continued

```
ATCAATTACG GGGTCATTAG TTCATAGCCC ATATATGGAG TTCCGCGTTA CATAACTTAC    2400

GGTAAATGGC CCGCCTGGCT GACCGCCCAA CGACCCCGC CCATTGACGT CAATAATGAC    2460

GTATGTTCCC ATAGTAACGC CAATAGGGAC TTTCCATTGA CGTCAATGGG TGGACTATTT    2520

ACGGTAAACT GCCCACTTGG CAGTACATCA AGTGTATCAT ATGCCAAGTA CGCCCCCTAT    2580

TGACGTCAAT GACGGTAAAT GGCCCGCCTG GCATTATGCC CAGTACATGA CCTTATGGGA    2640

CTTTCCTACT TGGCAGTACA TCTACGTATT AGTCATCGCT ATTACCATGG TGATGCGGTT    2700

TTGGCAGTAC ATCAATGGGC GTGGATAGCG GTTTGACTCA CGGGGATTTC CAAGTCTCCA    2760

CCCCATTGAC GTCAATGGGA GTTTGTTTTG GCACCAAAAT CAACGGGACT TTCCAAAATG    2820

TCGTAACAAC TCCGCCCCAT TGACGCAAAT GGGCGGTAGG CGTGTACGGT GGGAGGTCTA    2880

TATAAGCAGA GCTCATACTC GAGTATTTTA GAGAAGAATT AACCTTTTGC TTCTCCAGTT    2940

GAACATTTGT AGCAATAAGC CACC ATG GTT TAT GAG CTC TCC ACC TGC TTC      2991
                           Met Val Tyr Glu Leu Ser Thr Cys Phe
                            1                   5
```

| | | | | | | | | | | | | | | | | |
|---|---|---|---|---|---|---|---|---|---|---|---|---|---|---|---|---|
| TTT | CTG | TGC | CTT | TTG | CGA | TTC | TGC | TTT | AGT | GCC | ACC | AGA | AGA | TAC | TAC | 3039 |
| Phe | Leu | Cys | Leu | Leu | Arg | Phe | Cys | Phe | Ser | Ala | Thr | Arg | Arg | Tyr | Tyr | |
| 10 | | | | | 15 | | | | | 20 | | | | | 25 | |

| | | | | | | | | | | | | | | | | |
|---|---|---|---|---|---|---|---|---|---|---|---|---|---|---|---|---|
| CTG | GGT | GCA | GTG | GAA | CTG | TCA | TGG | GAC | TAT | ATG | CAA | AGT | GAT | CTC | GGT | 3087 |
| Leu | Gly | Ala | Val | Glu | Leu | Ser | Trp | Asp | Tyr | Met | Gln | Ser | Asp | Leu | Gly | |
| | | | | 30 | | | | | 35 | | | | | 40 | | |

| | | | | | | | | | | | | | | | | |
|---|---|---|---|---|---|---|---|---|---|---|---|---|---|---|---|---|
| GAG | CTG | CCT | GTG | GAC | GCA | AGA | TTT | CCT | CCT | AGA | GTG | CCA | AAA | TCT | TTT | 3135 |
| Glu | Leu | Pro | Val | Asp | Ala | Arg | Phe | Pro | Pro | Arg | Val | Pro | Lys | Ser | Phe | |
| | | | 45 | | | | | 50 | | | | | 55 | | | |

| | | | | | | | | | | | | | | | | |
|---|---|---|---|---|---|---|---|---|---|---|---|---|---|---|---|---|
| CCA | TTC | AAC | ACC | TCA | GTC | GTG | TAC | AAA | AAG | ACT | CTG | TTT | GTA | GAA | TTC | 3183 |
| Pro | Phe | Asn | Thr | Ser | Val | Val | Tyr | Lys | Lys | Thr | Leu | Phe | Val | Glu | Phe | |
| | | 60 | | | | | 65 | | | | | 70 | | | | |

| | | | | | | | | | | | | | | | | |
|---|---|---|---|---|---|---|---|---|---|---|---|---|---|---|---|---|
| ACG | GTT | CAC | CTT | TTC | AAC | ATC | GCT | AAG | CCA | AGG | CCA | CCC | TGG | ATG | GGT | 3231 |
| Thr | Val | His | Leu | Phe | Asn | Ile | Ala | Lys | Pro | Arg | Pro | Pro | Trp | Met | Gly | |
| 75 | | | | | 80 | | | | | 85 | | | | | | |

| | | | | | | | | | | | | | | | | |
|---|---|---|---|---|---|---|---|---|---|---|---|---|---|---|---|---|
| CTG | CTA | GGT | CCT | ACC | ATC | CAG | GCT | GAG | GTT | TAT | GAT | ACA | GTG | GTC | ATT | 3279 |
| Leu | Leu | Gly | Pro | Thr | Ile | Gln | Ala | Glu | Val | Tyr | Asp | Thr | Val | Val | Ile | |
| 90 | | | | | 95 | | | | | 100 | | | | | 105 | |

| | | | | | | | | | | | | | | | | |
|---|---|---|---|---|---|---|---|---|---|---|---|---|---|---|---|---|
| ACA | CTT | AAG | AAC | ATG | GCT | TCC | CAT | CCT | GTC | AGT | CTT | CAT | GCT | GTT | GGT | 3327 |
| Thr | Leu | Lys | Asn | Met | Ala | Ser | His | Pro | Val | Ser | Leu | His | Ala | Val | Gly | |
| | | | | 110 | | | | | 115 | | | | | 120 | | |

| | | | | | | | | | | | | | | | | |
|---|---|---|---|---|---|---|---|---|---|---|---|---|---|---|---|---|
| GTA | TCC | TAC | TGG | AAA | GCT | TCT | GAG | GGA | GCT | GAA | TAT | GAT | GAT | CAG | ACC | 3375 |
| Val | Ser | Tyr | Trp | Lys | Ala | Ser | Glu | Gly | Ala | Glu | Tyr | Asp | Asp | Gln | Thr | |
| | | | 125 | | | | | 130 | | | | | 135 | | | |

| | | | | | | | | | | | | | | | | |
|---|---|---|---|---|---|---|---|---|---|---|---|---|---|---|---|---|
| AGT | CAA | AGG | GAG | AAA | GAA | GAT | GAT | AAA | GTC | TTC | CCT | GGT | GGA | AGC | CAT | 3423 |
| Ser | Gln | Arg | Glu | Lys | Glu | Asp | Asp | Lys | Val | Phe | Pro | Gly | Gly | Ser | His | |
| | | 140 | | | | | 145 | | | | | 150 | | | | |

| | | | | | | | | | | | | | | | | |
|---|---|---|---|---|---|---|---|---|---|---|---|---|---|---|---|---|
| ACA | TAT | GTC | TGG | CAG | GTC | CTG | AAA | GAG | AAT | GGT | CCA | ATG | GCC | TCT | GAC | 3471 |
| Thr | Tyr | Val | Trp | Gln | Val | Leu | Lys | Glu | Asn | Gly | Pro | Met | Ala | Ser | Asp | |
| 155 | | | | | 160 | | | | | 165 | | | | | | |

| | | | | | | | | | | | | | | | | |
|---|---|---|---|---|---|---|---|---|---|---|---|---|---|---|---|---|
| CCA | CTG | TGC | CTT | ACC | TAC | TCA | TAT | CTT | TCT | CAT | GTG | GAC | CTG | GTA | AAA | 3519 |
| Pro | Leu | Cys | Leu | Thr | Tyr | Ser | Tyr | Leu | Ser | His | Val | Asp | Leu | Val | Lys | |
| 170 | | | | | 175 | | | | | 180 | | | | | 185 | |

| | | | | | | | | | | | | | | | | |
|---|---|---|---|---|---|---|---|---|---|---|---|---|---|---|---|---|
| GAC | TTG | AAT | TCA | GGC | CTC | ATT | GGA | GCC | CTA | CTA | GTA | TGT | AGA | GAA | GGG | 3567 |
| Asp | Leu | Asn | Ser | Gly | Leu | Ile | Gly | Ala | Leu | Leu | Val | Cys | Arg | Glu | Gly | |
| | | | | 190 | | | | | 195 | | | | | 200 | | |

| | | | | | | | | | | | | | | | | |
|---|---|---|---|---|---|---|---|---|---|---|---|---|---|---|---|---|
| AGT | CTG | GCC | AAG | GAA | AAG | ACA | CAG | ACC | TTG | CAC | AAA | TTT | ATA | CTA | CTT | 3615 |
| Ser | Leu | Ala | Lys | Glu | Lys | Thr | Gln | Thr | Leu | His | Lys | Phe | Ile | Leu | Leu | |
| | | | 205 | | | | | 210 | | | | | 215 | | | |

| | | | | | | | | | | | | | | | | |
|---|---|---|---|---|---|---|---|---|---|---|---|---|---|---|---|---|
| TTT | GCT | GTA | TTT | GAT | GAA | GGG | AAA | AGT | TGG | CAC | TCA | GAA | ACA | AAG | AAC | 3663 |
| Phe | Ala | Val | Phe | Asp | Glu | Gly | Lys | Ser | Trp | His | Ser | Glu | Thr | Lys | Asn | |
| | | 220 | | | | | 225 | | | | | 230 | | | | |

| | | | | | | | | | | | | | | | | |
|---|---|---|---|---|---|---|---|---|---|---|---|---|---|---|---|---|
| TCC | TTG | ATG | CAG | GAT | AGG | GAT | GCT | GCA | TCT | GCT | CGG | GCC | TGG | CCT | AAA | 3711 |
| Ser | Leu | Met | Gln | Asp | Arg | Asp | Ala | Ala | Ser | Ala | Arg | Ala | Trp | Pro | Lys | |
| | 235 | | | | 240 | | | | | 245 | | | | | | |
| ATG | CAC | ACA | GTC | AAT | GGT | TAT | GTA | AAC | AGG | TCT | CTG | CCA | GGT | CTG | ATT | 3759 |
| Met | His | Thr | Val | Asn | Gly | Tyr | Val | Asn | Arg | Ser | Leu | Pro | Gly | Leu | Ile | |
| 250 | | | | | 255 | | | | | 260 | | | | | 265 | |
| GGA | TGC | CAC | AGG | AAA | TCA | GTC | TAT | TGG | CAT | GTG | ATT | GGA | ATG | GGC | ACC | 3807 |
| Gly | Cys | His | Arg | Lys | Ser | Val | Tyr | Trp | His | Val | Ile | Gly | Met | Gly | Thr | |
| | | | | 270 | | | | | 275 | | | | | | 280 | |
| ACT | CCT | GAA | GTG | CAC | TCA | ATA | TTC | CTC | GAA | GGT | CAC | ACA | TTT | CTT | GTG | 3855 |
| Thr | Pro | Glu | Val | His | Ser | Ile | Phe | Leu | Glu | Gly | His | Thr | Phe | Leu | Val | |
| | | | 285 | | | | | 290 | | | | | 295 | | | |
| AGG | AAC | CAT | CGC | CAG | GCG | TCC | TTG | GAA | ATC | TCG | CCA | ATA | ACT | TTC | CTT | 3903 |
| Arg | Asn | His | Arg | Gln | Ala | Ser | Leu | Glu | Ile | Ser | Pro | Ile | Thr | Phe | Leu | |
| | | 300 | | | | | 305 | | | | | 310 | | | | |
| ACT | GCT | CAA | ACA | CTC | TTG | ATG | GAC | CTT | GGA | CAG | TTT | CTA | CTG | TTT | TGT | 3951 |
| Thr | Ala | Gln | Thr | Leu | Leu | Met | Asp | Leu | Gly | Gln | Phe | Leu | Leu | Phe | Cys | |
| | 315 | | | | | 320 | | | | | 325 | | | | | |
| CAT | ATC | TCT | TCC | CAC | CAA | CAT | GAT | GGC | ATG | GAA | GCT | TAT | GTC | AAA | GTA | 3999 |
| His | Ile | Ser | Ser | His | Gln | His | Asp | Gly | Met | Glu | Ala | Tyr | Val | Lys | Val | |
| 330 | | | | | 335 | | | | | 340 | | | | | 345 | |
| GAC | AGC | TGT | CCA | GAG | GAA | CCC | CAA | CTA | CGA | ATG | AAA | AAT | AAT | GAA | GAA | 4047 |
| Asp | Ser | Cys | Pro | Glu | Glu | Pro | Gln | Leu | Arg | Met | Lys | Asn | Asn | Glu | Glu | |
| | | | | 350 | | | | | 355 | | | | | 360 | | |
| GCG | GAA | GAC | TAT | GAT | GAT | GAT | CTT | ACT | GAT | TCT | GAA | ATG | GAT | GTG | GTC | 4095 |
| Ala | Glu | Asp | Tyr | Asp | Asp | Asp | Leu | Thr | Asp | Ser | Glu | Met | Asp | Val | Val | |
| | | | 365 | | | | | 370 | | | | | 375 | | | |
| AGG | TTT | GAT | GAT | GAC | AAC | TCT | CCT | TCC | TTT | ATC | CAA | ATT | CGC | TCA | GTT | 4143 |
| Arg | Phe | Asp | Asp | Asp | Asn | Ser | Pro | Ser | Phe | Ile | Gln | Ile | Arg | Ser | Val | |
| | | 380 | | | | | 385 | | | | | 390 | | | | |
| GCC | AAG | AAG | CAT | CCT | AAA | ACT | TGG | GTA | CAT | TAC | ATT | GCT | GCT | GAA | GAG | 4191 |
| Ala | Lys | Lys | His | Pro | Lys | Thr | Trp | Val | His | Tyr | Ile | Ala | Ala | Glu | Glu | |
| | 395 | | | | | 400 | | | | | 405 | | | | | |
| GAG | GAC | TGG | GAC | TAT | GCT | CCC | TTA | GTC | CTC | GCC | CCC | GAT | GAC | AGA | AGT | 4239 |
| Glu | Asp | Trp | Asp | Tyr | Ala | Pro | Leu | Val | Leu | Ala | Pro | Asp | Asp | Arg | Ser | |
| 410 | | | | | 415 | | | | | 420 | | | | | 425 | |
| TAT | AAA | AGT | CAA | TAT | TTG | AAC | AAT | GGC | CCT | CAG | CGG | ATT | GGT | AGG | AAG | 4287 |
| Tyr | Lys | Ser | Gln | Tyr | Leu | Asn | Asn | Gly | Pro | Gln | Arg | Ile | Gly | Arg | Lys | |
| | | | | 430 | | | | | 435 | | | | | 440 | | |
| TAC | AAA | AAA | GTC | CGA | TTT | ATG | GCA | TAC | ACA | GAT | GAA | ACC | TTT | AAG | ACT | 4335 |
| Tyr | Lys | Lys | Val | Arg | Phe | Met | Ala | Tyr | Thr | Asp | Glu | Thr | Phe | Lys | Thr | |
| | | | 445 | | | | | 450 | | | | | 455 | | | |
| CGT | GAA | GCT | ATT | CAG | CAT | GAA | TCA | GGA | ATC | TTG | GGA | CCT | TTA | CTT | TAT | 4383 |
| Arg | Glu | Ala | Ile | Gln | His | Glu | Ser | Gly | Ile | Leu | Gly | Pro | Leu | Leu | Tyr | |
| | | 460 | | | | | 465 | | | | | 470 | | | | |
| GGG | GAA | GTT | GGA | GAC | ACA | CTG | TTG | ATT | ATA | TTT | AAG | AAT | CAA | GCA | AGC | 4431 |
| Gly | Glu | Val | Gly | Asp | Thr | Leu | Leu | Ile | Ile | Phe | Lys | Asn | Gln | Ala | Ser | |
| | 475 | | | | | 480 | | | | | 485 | | | | | |
| AGA | CCA | TAT | AAC | ATC | TAC | CCT | CAC | GGA | ATC | ACT | GAT | GTC | CGT | CCT | TTG | 4479 |
| Arg | Pro | Tyr | Asn | Ile | Tyr | Pro | His | Gly | Ile | Thr | Asp | Val | Arg | Pro | Leu | |
| 490 | | | | | 495 | | | | | 500 | | | | | 505 | |
| TAT | TCA | AGG | AGA | TTA | CCA | AAA | GGT | GTA | AAA | CAT | TTG | AAG | GAT | TTT | CCA | 4527 |
| Tyr | Ser | Arg | Arg | Leu | Pro | Lys | Gly | Val | Lys | His | Leu | Lys | Asp | Phe | Pro | |
| | | | | 510 | | | | | 515 | | | | | 520 | | |
| ATT | CTG | CCA | GGA | GAA | ATA | TTC | AAA | TAT | AAA | TGG | ACA | GTG | ACT | GTA | GAA | 4575 |
| Ile | Leu | Pro | Gly | Glu | Ile | Phe | Lys | Tyr | Lys | Trp | Thr | Val | Thr | Val | Glu | |
| | | | 525 | | | | | 530 | | | | | 535 | | | |
| GAT | GGG | CCA | ACT | AAA | TCA | GAT | CCT | CGG | TGC | CTG | ACC | CGC | TAT | TAC | TCT | 4623 |
| Asp | Gly | Pro | Thr | Lys | Ser | Asp | Pro | Arg | Cys | Leu | Thr | Arg | Tyr | Tyr | Ser | |
| | | 540 | | | | | 545 | | | | | 550 | | | | |

| | | | | | | | | | | | | | | | | |
|---|---|---|---|---|---|---|---|---|---|---|---|---|---|---|---|---|
| AGT | TTC | GTT | AAT | ATG | GAG | AGA | GAT | CTA | GCT | TCA | GGA | CTC | ATT | GGC | CCT | 4671 |
| Ser | Phe | Val | Asn | Met | Glu | Arg | Asp | Leu | Ala | Ser | Gly | Leu | Ile | Gly | Pro | |
| | 555 | | | | 560 | | | | | 565 | | | | | | |
| CTC | CTC | ATC | TGC | TAC | AAA | GAA | TCT | GTA | GAT | CAA | AGA | GGA | AAC | CAG | ATA | 4719 |
| Leu | Leu | Ile | Cys | Tyr | Lys | Glu | Ser | Val | Asp | Gln | Arg | Gly | Asn | Gln | Ile | |
| 570 | | | | | 575 | | | | | 580 | | | | | 585 | |
| ATG | TCA | GAC | AAG | AGG | AAT | GTC | ATC | CTG | TTT | TCT | GTA | TTT | GAT | GAG | AAC | 4767 |
| Met | Ser | Asp | Lys | Arg | Asn | Val | Ile | Leu | Phe | Ser | Val | Phe | Asp | Glu | Asn | |
| | | | | 590 | | | | | 595 | | | | | | 600 | |
| CGA | AGC | TGG | TAC | CTC | ACA | GAG | AAT | ATA | CAA | CGC | TTT | CTC | CCC | AAT | CCA | 4815 |
| Arg | Ser | Trp | Tyr | Leu | Thr | Glu | Asn | Ile | Gln | Arg | Phe | Leu | Pro | Asn | Pro | |
| | | | 605 | | | | | 610 | | | | | 615 | | | |
| GCT | GGA | GTG | CAG | CTT | GAG | GAT | CCA | GAG | TTC | CAA | GCC | TCC | AAC | ATC | ATG | 4863 |
| Ala | Gly | Val | Gln | Leu | Glu | Asp | Pro | Glu | Phe | Gln | Ala | Ser | Asn | Ile | Met | |
| | | | 620 | | | | | 625 | | | | | 630 | | | |
| CAC | AGC | ATC | AAT | GGC | TAT | GTT | TTT | GAT | AGT | TTG | CAG | TTG | TCA | GTT | TGT | 4911 |
| His | Ser | Ile | Asn | Gly | Tyr | Val | Phe | Asp | Ser | Leu | Gln | Leu | Ser | Val | Cys | |
| | 635 | | | | | 640 | | | | | 645 | | | | | |
| TTG | CAT | GAG | GTG | GCA | TAC | TGG | TAC | ATT | CTA | AGC | ATT | GGA | GCA | CAG | ACT | 4959 |
| Leu | His | Glu | Val | Ala | Tyr | Trp | Tyr | Ile | Leu | Ser | Ile | Gly | Ala | Gln | Thr | |
| 650 | | | | | 655 | | | | | 660 | | | | | 665 | |
| GAC | TTC | CTT | TCT | GTC | TTC | TTC | TCT | GGA | TAT | ACC | TTC | AAA | CAC | AAA | ATG | 5007 |
| Asp | Phe | Leu | Ser | Val | Phe | Phe | Ser | Gly | Tyr | Thr | Phe | Lys | His | Lys | Met | |
| | | | | 670 | | | | | 675 | | | | | | 680 | |
| GTC | TAT | GAA | GAC | ACA | CTC | ACC | CTA | TTC | CCA | TTC | TCA | GGA | GAA | ACT | GTC | 5055 |
| Val | Tyr | Glu | Asp | Thr | Leu | Thr | Leu | Phe | Pro | Phe | Ser | Gly | Glu | Thr | Val | |
| | | | 685 | | | | | 690 | | | | | 695 | | | |
| TTC | ATG | TCG | ATG | GAA | AAC | CCA | GGT | CTA | TGG | ATT | CTG | GGG | TGC | CAC | AAC | 5103 |
| Phe | Met | Ser | Met | Glu | Asn | Pro | Gly | Leu | Trp | Ile | Leu | Gly | Cys | His | Asn | |
| | | 700 | | | | | 705 | | | | | 710 | | | | |
| TCA | GAC | TTT | CGG | AAC | AGA | GGC | ATG | ACC | GCC | TTA | CTG | AAG | GTT | TCT | AGT | 5151 |
| Ser | Asp | Phe | Arg | Asn | Arg | Gly | Met | Thr | Ala | Leu | Leu | Lys | Val | Ser | Ser | |
| | 715 | | | | | 720 | | | | | 725 | | | | | |
| TGT | GAC | AAG | AAC | ACT | GGT | GAT | TAT | TAC | GAG | GAC | AGT | TAT | GAA | GAT | ATT | 5199 |
| Cys | Asp | Lys | Asn | Thr | Gly | Asp | Tyr | Tyr | Glu | Asp | Ser | Tyr | Glu | Asp | Ile | |
| 730 | | | | | 735 | | | | | 740 | | | | | 745 | |
| TCA | GCA | TAC | TTG | CTG | AGT | AAA | AAC | AAT | GCC | ATT | GAA | CCA | AGA | AGC | TTC | 5247 |
| Ser | Ala | Tyr | Leu | Leu | Ser | Lys | Asn | Asn | Ala | Ile | Glu | Pro | Arg | Ser | Phe | |
| | | | | 750 | | | | | 755 | | | | | | 760 | |
| TCC | CAG | AAT | TCA | AGA | CAC | CCT | AGC | ACT | AGG | CAA | AAG | CAA | TTT | AAT | GCC | 5295 |
| Ser | Gln | Asn | Ser | Arg | His | Pro | Ser | Thr | Arg | Gln | Lys | Gln | Phe | Asn | Ala | |
| | | | 765 | | | | | 770 | | | | | 775 | | | |
| ACC | CCA | CCA | GTC | TTG | AAA | CGC | CAT | CAA | CGG | GAA | ATA | ACT | CGT | ACT | ACT | 5343 |
| Thr | Pro | Pro | Val | Leu | Lys | Arg | His | Gln | Arg | Glu | Ile | Thr | Arg | Thr | Thr | |
| | | 780 | | | | | 785 | | | | | 790 | | | | |
| CTT | CAG | TCA | GAT | CAA | GAG | GAA | ATT | GAC | TAT | GAT | GAT | ACC | ATA | TCA | GTT | 5391 |
| Leu | Gln | Ser | Asp | Gln | Glu | Glu | Ile | Asp | Tyr | Asp | Asp | Thr | Ile | Ser | Val | |
| | 795 | | | | | 800 | | | | | 805 | | | | | |
| GAA | ATG | AAG | AAG | GAA | GAT | TTT | GAC | ATT | TAT | GAT | GAG | GAT | GAA | AAT | CAG | 5439 |
| Glu | Met | Lys | Lys | Glu | Asp | Phe | Asp | Ile | Tyr | Asp | Glu | Asp | Glu | Asn | Gln | |
| 810 | | | | | 815 | | | | | 820 | | | | | 825 | |
| AGC | CCC | CGC | AGC | TTT | CAA | AAG | AAA | ACA | CGA | CAC | TAT | TTT | ATT | GCT | GCA | 5487 |
| Ser | Pro | Arg | Ser | Phe | Gln | Lys | Lys | Thr | Arg | His | Tyr | Phe | Ile | Ala | Ala | |
| | | | | 830 | | | | | 835 | | | | | | 840 | |
| GTG | GAG | AGG | CTC | TGG | GAT | TAT | GGG | ATG | AGT | AGC | TCC | CCA | CAT | GTT | CTA | 5535 |
| Val | Glu | Arg | Leu | Trp | Asp | Tyr | Gly | Met | Ser | Ser | Ser | Pro | His | Val | Leu | |
| | | | 845 | | | | | 850 | | | | | 855 | | | |
| AGA | AAC | AGG | GCT | CAG | AGT | GGC | AGT | GTC | CCT | CAG | TTC | AAG | AAA | GTT | GTT | 5583 |
| Arg | Asn | Arg | Ala | Gln | Ser | Gly | Ser | Val | Pro | Gln | Phe | Lys | Lys | Val | Val | |
| | | 860 | | | | | 865 | | | | | 870 | | | | |

| | | | | | | | | | | | | | | | | |
|---|---|---|---|---|---|---|---|---|---|---|---|---|---|---|---|---|
| TTC | CAG | GAA | TTT | ACT | GAT | GGC | TCC | TTT | ACT | CAG | CCC | TTA | TAC | CGT | GGA | 5631 |
| Phe | Gln | Glu | Phe | Thr | Asp | Gly | Ser | Phe | Thr | Gln | Pro | Leu | Tyr | Arg | Gly | |
| | 875 | | | | 880 | | | | | 885 | | | | | | |
| GAA | CTA | AAT | GAA | CAT | TTG | GGA | CTC | CTG | GGG | CCA | TAT | ATA | AGA | GCA | GAA | 5679 |
| Glu | Leu | Asn | Glu | His | Leu | Gly | Leu | Leu | Gly | Pro | Tyr | Ile | Arg | Ala | Glu | |
| 890 | | | | | 895 | | | | | 900 | | | | | 905 | |
| GTT | GAA | GAT | AAT | ATC | ATG | GTA | ACT | TTC | AGA | AAT | CAG | GCC | TCT | CGT | CCC | 5727 |
| Val | Glu | Asp | Asn | Ile | Met | Val | Thr | Phe | Arg | Asn | Gln | Ala | Ser | Arg | Pro | |
| | | | 910 | | | | | | 915 | | | | | 920 | | |
| TAT | TCC | TTC | TAT | TCT | AGC | CTT | ATT | TCT | TAT | GAG | GAA | GAT | CAG | AGG | CAA | 5775 |
| Tyr | Ser | Phe | Tyr | Ser | Ser | Leu | Ile | Ser | Tyr | Glu | Glu | Asp | Gln | Arg | Gln | |
| | | | 925 | | | | | 930 | | | | | 935 | | | |
| GGA | GCA | GAA | CCT | AGA | AAA | AAC | TTT | GTC | AAG | CCT | AAT | GAA | ACC | AAA | ACT | 5823 |
| Gly | Ala | Glu | Pro | Arg | Lys | Asn | Phe | Val | Lys | Pro | Asn | Glu | Thr | Lys | Thr | |
| | | 940 | | | | | 945 | | | | | 950 | | | | |
| TAC | TTT | TGG | AAA | GTG | CAA | CAT | CAT | ATG | GCA | CCC | ACT | AAA | GAT | GAG | TTT | 5871 |
| Tyr | Phe | Trp | Lys | Val | Gln | His | His | Met | Ala | Pro | Thr | Lys | Asp | Glu | Phe | |
| | 955 | | | | | 960 | | | | | 965 | | | | | |
| GAC | TGC | AAA | GCC | TGG | GCT | TAT | TTC | TCT | GAT | GTT | GAC | CTG | GAA | AAA | GAT | 5919 |
| Asp | Cys | Lys | Ala | Trp | Ala | Tyr | Phe | Ser | Asp | Val | Asp | Leu | Glu | Lys | Asp | |
| 970 | | | | 975 | | | | | 980 | | | | | | 985 | |
| GTG | CAC | TCA | GGC | CTG | ATT | GGA | CCC | CTT | CTG | GTC | TGC | CAC | ACT | AAC | ACA | 5967 |
| Val | His | Ser | Gly | Leu | Ile | Gly | Pro | Leu | Leu | Val | Cys | His | Thr | Asn | Thr | |
| | | | | 990 | | | | | 995 | | | | | | 1000 | |
| CTG | AAC | CCT | GCT | CAT | GGG | AGA | CAA | GTG | ACA | GTA | CAG | GAA | TTT | GCT | CTG | 6015 |
| Leu | Asn | Pro | Ala | His | Gly | Arg | Gln | Val | Thr | Val | Gln | Glu | Phe | Ala | Leu | |
| | | | | 1005 | | | | | 1010 | | | | | 1015 | | |
| TTT | TTC | ACC | ATC | TTT | GAT | GAG | ACC | AAA | AGC | TGG | TAC | TTC | ACT | GAA | AAT | 6063 |
| Phe | Phe | Thr | Ile | Phe | Asp | Glu | Thr | Lys | Ser | Trp | Tyr | Phe | Thr | Glu | Asn | |
| | | | 1020 | | | | | 1025 | | | | | 1030 | | | |
| ATG | GAA | AGA | AAC | TGC | AGG | GCT | CCC | TGC | AAT | ATC | CAG | ATG | GAA | GAT | CCC | 6111 |
| Met | Glu | Arg | Asn | Cys | Arg | Ala | Pro | Cys | Asn | Ile | Gln | Met | Glu | Asp | Pro | |
| | | 1035 | | | | | 1040 | | | | | 1045 | | | | |
| ACT | TTT | AAA | GAG | AAT | TAT | CGC | TTC | CAT | GCA | ATC | AAT | GGC | TAC | ATA | ATG | 6159 |
| Thr | Phe | Lys | Glu | Asn | Tyr | Arg | Phe | His | Ala | Ile | Asn | Gly | Tyr | Ile | Met | |
| 1050 | | | | | 1055 | | | | | 1060 | | | | | 1065 | |
| GAT | ACA | CTA | CCT | GGC | TTA | GTA | ATG | GCT | CAG | GAT | CAA | AGG | ATT | CGA | TGG | 6207 |
| Asp | Thr | Leu | Pro | Gly | Leu | Val | Met | Ala | Gln | Asp | Gln | Arg | Ile | Arg | Trp | |
| | | | | 1070 | | | | | 1075 | | | | | 1080 | | |
| TAT | CTG | CTC | AGC | ATG | GGC | AGC | AAT | GAA | AAC | ATC | CAT | TCT | ATT | CAT | TTC | 6255 |
| Tyr | Leu | Leu | Ser | Met | Gly | Ser | Asn | Glu | Asn | Ile | His | Ser | Ile | His | Phe | |
| | | | | 1085 | | | | | 1090 | | | | | 1095 | | |
| AGT | GGA | CAT | GTG | TTC | ACT | GTA | CGA | AAA | AAA | GAG | GAG | TAT | AAA | ATG | GCA | 6303 |
| Ser | Gly | His | Val | Phe | Thr | Val | Arg | Lys | Lys | Glu | Glu | Tyr | Lys | Met | Ala | |
| | | | 1100 | | | | | 1105 | | | | | 1110 | | | |
| CTG | TAC | AAT | CTC | TAT | CCA | GGT | GTT | TTT | GAG | ACA | GTG | GAA | ATG | TTA | CCA | 6351 |
| Leu | Tyr | Asn | Leu | Tyr | Pro | Gly | Val | Phe | Glu | Thr | Val | Glu | Met | Leu | Pro | |
| | | 1115 | | | | | 1120 | | | | | 1125 | | | | |
| TCC | AAA | GCT | GGA | ATT | TGG | CGG | GTG | GAA | TGC | CTT | ATT | GGC | GAG | CAT | CTA | 6399 |
| Ser | Lys | Ala | Gly | Ile | Trp | Arg | Val | Glu | Cys | Leu | Ile | Gly | Glu | His | Leu | |
| 1130 | | | | | 1135 | | | | | 1140 | | | | | 1145 | |
| CAT | GCT | GGG | ATG | AGC | ACA | CTT | TTT | CTG | GTG | TAC | AGC | AAT | AAG | TGT | CAG | 6447 |
| His | Ala | Gly | Met | Ser | Thr | Leu | Phe | Leu | Val | Tyr | Ser | Asn | Lys | Cys | Gln | |
| | | | | 1150 | | | | | 1155 | | | | | 1160 | | |
| ACT | CCC | CTG | GGA | ATG | GCT | TCT | GGA | CAC | ATT | AGA | GAT | TTT | CAG | ATT | ACA | 6495 |
| Thr | Pro | Leu | Gly | Met | Ala | Ser | Gly | His | Ile | Arg | Asp | Phe | Gln | Ile | Thr | |
| | | | 1165 | | | | | 1170 | | | | | 1175 | | | |
| GCT | TCA | GGA | CAA | TAT | GGA | CAG | TGG | GCC | CCA | AAG | CTG | GCC | AGA | CTT | CAT | 6543 |
| Ala | Ser | Gly | Gln | Tyr | Gly | Gln | Trp | Ala | Pro | Lys | Leu | Ala | Arg | Leu | His | |
| | | 1180 | | | | | 1185 | | | | | 1190 | | | | |

| | | | | | | | | | | | | | | | | |
|---|---|---|---|---|---|---|---|---|---|---|---|---|---|---|---|---|
| TAT | TCC | GGA | TCA | ATC | AAT | GCC | TGG | AGC | ACC | AAG | GAG | CCC | TTT | TCT | TGG | 6591 |
| Tyr | Ser | Gly | Ser | Ile | Asn | Ala | Trp | Ser | Thr | Lys | Glu | Pro | Phe | Ser | Trp | |
| | | | 1195 | | | | 1200 | | | | 1205 | | | | | |
| ATC | AAG | GTG | GAT | CTG | TTG | GCA | CCA | ATG | ATT | ATT | CAC | GGC | ATC | AAG | ACC | 6639 |
| Ile | Lys | Val | Asp | Leu | Leu | Ala | Pro | Met | Ile | Ile | His | Gly | Ile | Lys | Thr | |
| 1210 | | | | 1215 | | | | 1220 | | | | | | | 1225 | |
| CAG | GGT | GCC | CGT | CAG | AAG | TTC | TCC | AGC | CTC | TAC | ATC | TCT | CAG | TTT | ATC | 6687 |
| Gln | Gly | Ala | Arg | Gln | Lys | Phe | Ser | Ser | Leu | Tyr | Ile | Ser | Gln | Phe | Ile | |
| | | | | 1230 | | | | | 1235 | | | | | 1240 | | |
| ATC | ATG | TAT | AGT | CTT | GAT | GGG | AAG | AAG | TGG | CAG | ACT | TAT | CGA | GGA | AAT | 6735 |
| Ile | Met | Tyr | Ser | Leu | Asp | Gly | Lys | Lys | Trp | Gln | Thr | Tyr | Arg | Gly | Asn | |
| | | | 1245 | | | | | 1250 | | | | | 1255 | | | |
| TCC | ACT | GGA | ACC | TTA | ATG | GTC | TTC | TTT | GGC | AAT | GTG | GAT | TCA | TCT | GGG | 6783 |
| Ser | Thr | Gly | Thr | Leu | Met | Val | Phe | Phe | Gly | Asn | Val | Asp | Ser | Ser | Gly | |
| | | 1260 | | | | | 1265 | | | | | 1270 | | | | |
| ATA | AAA | CAC | AAT | ATT | TTT | AAC | CCT | CCA | ATT | ATT | GCT | CGA | TAC | ATC | CGT | 6831 |
| Ile | Lys | His | Asn | Ile | Phe | Asn | Pro | Pro | Ile | Ile | Ala | Arg | Tyr | Ile | Arg | |
| | 1275 | | | | | 1280 | | | | | 1285 | | | | | |
| TTG | CAC | CCA | ACT | CAT | TAT | AGC | ATT | CGC | AGC | ACT | CTT | CGC | ATG | GAG | TTG | 6879 |
| Leu | His | Pro | Thr | His | Tyr | Ser | Ile | Arg | Ser | Thr | Leu | Arg | Met | Glu | Leu | |
| 1290 | | | | | 1295 | | | | | 1300 | | | | | 1305 | |
| ATG | GGC | TGT | GAT | TTA | AAT | AGT | TGC | AGC | ATG | CCA | TTG | GGA | ATG | GAG | AGT | 6927 |
| Met | Gly | Cys | Asp | Leu | Asn | Ser | Cys | Ser | Met | Pro | Leu | Gly | Met | Glu | Ser | |
| | | | | 1310 | | | | | 1315 | | | | | 1320 | | |
| AAA | GCA | ATA | TCA | GAT | GCA | CAG | ATT | ACT | GCT | TCA | TCC | TAC | TTT | ACC | AAT | 6975 |
| Lys | Ala | Ile | Ser | Asp | Ala | Gln | Ile | Thr | Ala | Ser | Ser | Tyr | Phe | Thr | Asn | |
| | | | 1325 | | | | | 1330 | | | | | 1335 | | | |
| ATG | TTT | GCC | ACC | TGG | TCT | CCT | TCA | AAA | GCT | CGA | CTT | CAC | CTC | CAA | GGG | 7023 |
| Met | Phe | Ala | Thr | Trp | Ser | Pro | Ser | Lys | Ala | Arg | Leu | His | Leu | Gln | Gly | |
| | | | 1340 | | | | | 1345 | | | | | 1350 | | | |
| AGG | AGT | AAT | GCC | TGG | AGA | CCT | CAG | GTG | AAT | AAT | CCA | AAA | GAG | TGG | CTG | 7071 |
| Arg | Ser | Asn | Ala | Trp | Arg | Pro | Gln | Val | Asn | Asn | Pro | Lys | Glu | Trp | Leu | |
| | | 1355 | | | | | 1360 | | | | | 1365 | | | | |
| CAA | GTG | GAC | TTC | CAG | AAG | ACA | ATG | AAA | GTC | ACA | GGA | GTA | ACT | ACT | CAG | 7119 |
| Gln | Val | Asp | Phe | Gln | Lys | Thr | Met | Lys | Val | Thr | Gly | Val | Thr | Thr | Gln | |
| 1370 | | | | | 1375 | | | | | 1380 | | | | | 1385 | |
| GGA | GTA | AAA | TCT | CTG | CTT | ACC | AGC | ATG | TAT | GTG | AAG | GAG | TTC | CTC | ATC | 7167 |
| Gly | Val | Lys | Ser | Leu | Leu | Thr | Ser | Met | Tyr | Val | Lys | Glu | Phe | Leu | Ile | |
| | | | | 1390 | | | | | 1395 | | | | | 1400 | | |
| TCC | AGC | AGT | CAA | GAT | GGC | CAT | CAG | TGG | ACT | CTC | TTT | TTT | CAG | AAT | GGC | 7215 |
| Ser | Ser | Ser | Gln | Asp | Gly | His | Gln | Trp | Thr | Leu | Phe | Phe | Gln | Asn | Gly | |
| | | | 1405 | | | | | 1410 | | | | | 1415 | | | |
| AAA | GTA | AAG | GTT | TTT | CAG | GGA | AAT | CAA | GAC | TCC | TTC | ACA | CCT | GTG | GTG | 7263 |
| Lys | Val | Lys | Val | Phe | Gln | Gly | Asn | Gln | Asp | Ser | Phe | Thr | Pro | Val | Val | |
| | 1420 | | | | | 1425 | | | | | 1430 | | | | | |
| AAC | TCT | CTA | GAC | CCA | CCG | TTA | CTG | ACT | CGC | TAC | CTT | CGA | ATT | CAC | CCC | 7311 |
| Asn | Ser | Leu | Asp | Pro | Pro | Leu | Leu | Thr | Arg | Tyr | Leu | Arg | Ile | His | Pro | |
| | 1435 | | | | | 1440 | | | | | 1445 | | | | | |
| CAG | AGT | TGG | GTG | CAC | CAG | ATT | GCC | CTG | AGG | ATG | GAG | GTT | CTG | GGC | TGC | 7359 |
| Gln | Ser | Trp | Val | His | Gln | Ile | Ala | Leu | Arg | Met | Glu | Val | Leu | Gly | Cys | |
| 1450 | | | | 1455 | | | | | 1460 | | | | | 1465 | | |
| GAG | GCA | CAG | GAC | CTC | TAC | T GAGGGTGGCC ACTGCAGCAC CTGCCACTGC | | | | | | | | | | 7408 |
| Glu | Ala | Gln | Asp | Leu | Tyr | | | | | | | | | | | |
| | | | | 1470 | | | | | | | | | | | | |

| | | | | |
|---|---|---|---|---|
| CGTCACCTCT | CCCTCCTCAG | CTCCAGGGCA | GTGTCCCTCC | CTGGCTTGCC TTCTACCTTT | 7468 |
| GTGCTAAATC | CTAGCAGACA | CTGCCTTGAA | GCCTCCTGAA | TTAACTATCA TCAGTCCTGC | 7528 |
| ATTTCTTTGG | TGGGGGGCCA | GGAGGGTGCA | TCCAATTTAA | CTTAACTCTT ACCTATTTTC | 7588 |
| TGCAGGGGAT | CTCAGTCGAG | CACCTTTCTA | AGTAAACAGT | ACATGAACCT TTACCCCGTT | 7648 |

| | | | | | |
|---|---|---|---|---|---|
| GCTCGGCAAC | GGCCTGGTCT | GTGCCAAGTG | TTTGCTGACG | CAACCCCCAC | TGGCTGGGGC | 7708 |
| TTGGCCATAG | GCCATCAGCG | CATGCGTGGA | ACCTTTGTGG | CTCCTCTGCC | GATCCATACT | 7768 |
| GCGGAACTCC | TAGCCGCTTG | TTTTGCTCGC | AGCCGGTCTG | GAGCAAAGCT | CATCGGAACT | 7828 |
| GACAATTCTG | TCGTCCTCTC | GCGGAAATAT | ACATCGTTTC | CATGGCTGCT | AGGCTGTACT | 7888 |
| GCCAACTGGA | TCCTTCGCGG | GACGTCCTTT | GTTACGTCC | CGTCGGCGCT | GAATCCCGCG | 7948 |
| GACGACCCCT | CTCGGGGCCG | CTTGGGACTC | TCTCGTCCCC | TTCTCCGTCT | GCCGTTCCAG | 8008 |
| CCGACCACGG | GGCGCACCTC | TCTTTACGCG | GTCTCCCGT | CTGTGCCTTC | TCATCTGCCG | 8068 |
| GTCCGTGTGC | ACTTCGCTTC | ACCTCTGCAC | GTTGCATGGA | GACCACCGTG | AACGCCCATC | 8128 |
| AGATCCTGCC | CAAGGTCTTA | CATAAGAGGA | CTCTTGGACT | CCCAGCAATG | TCAACGACCG | 8188 |
| ACCTTGAGGA | ATTAATTGTT | GTTGTTAACT | TGTTTATTGC | AGCTTATAAT | GGTTACAAAT | 8248 |
| AAAGCAATAG | CATCACAAAT | TTCACAAATA | AAGCATTTTT | TTCACTGCAT | TCTAGTTGTG | 8308 |
| GTTTGTCCAA | ACTCATCAAT | GTATCTTATC | ATGTCTGGAT | CATCCCGCCA | TGGTATCAAC | 8368 |
| GCCATATTTC | TATTTACAGT | AGGGACCTCT | TCGTTGTGTA | GGTACCGCTG | TATTCCTAGG | 8428 |
| GAAATAGTAG | AGGCACCTTG | AACTGTCTGC | ATCAGCCATA | TAGCCCCGC | TGTTCGACTT | 8488 |
| ACAAACACAG | GCACAGTACT | GACAAACCCA | TACACCTCCT | CTGAAATACC | CATAGTTGCT | 8548 |
| AGGGCTGTCT | CCGAACTCAT | TACACCCTCC | AAAGTCAGAG | CTGTAATTTC | GCCATCAAGG | 8608 |
| GCAGCGAGGG | CTTCTCCAGA | TAAAATAGCT | TCTGCCGAGA | GTCCCGTAAG | GGTAGACACT | 8668 |
| TCAGCTAATC | CCTCGATGAG | GTCTACTAGA | ATAGTCAGTG | CGGCTCCCAT | TTTGAAAATT | 8728 |
| CACTTACTTG | ATCAGCTTCA | GAAGATGGCG | GAGGGCCTCC | AACACAGTAA | TTTTCCTCCC | 8788 |
| GACTCTTAAA | ATAGAAAATG | TCAAGTCAGT | TAAGCAGGAA | GTGGACTAAC | TGACGCAGCT | 8848 |
| GGCCGTGCGA | CATCCTCTTT | TAATTAGTTG | CTAGGCAACG | CCCTCCAGAG | GGCGTGTGGT | 8908 |
| TTTGCAAGAG | GAAGCAAAAG | CCTCTCCACC | CAGGCCTAGA | ATGTTCCAC | CCAATCATTA | 8968 |
| CTATGACAAC | AGCTGTTTTT | TTTAGTATTA | AGCAGAGGCC | GGGGACCCCT | GGGCCCGCTT | 9028 |
| ACTCTGGAGA | AAAAGAAGAG | AGGCATTGTA | GAGGCTTCCA | GAGGCAACTT | GTCAAAACAG | 9088 |
| GACTGCTTCT | ATTTCTGTCA | CACTGTCTGG | CCCTGTCACA | AGGTCCAGCA | CCTCCATACC | 9148 |
| CCCTTTAATA | AGCAGTTTGG | GAACGGGTGC | GGGTCTTACT | CCGCCCATCC | CGCCCCTAAC | 9208 |
| TCCGCCCAGT | TCCGCCCATT | CTCCGCCCCA | TGGCTGACTA | ATTTTTTTA | TTTATGCAGA | 9268 |
| GGCCGAGGCC | GCCTCGGCCT | CTGAGCTATT | CCAGAAGTAG | TGAGGAGGCT | TTTTTGGAGG | 9328 |
| CCTAGGCTTT | TGCAAAAAGC | TAATTC | | | | 9354 |

(2) INFORMATION FOR SEQ ID NO:3:

(i) SEQUENCE CHARACTERISTICS:
        (A) LENGTH: 1471 amino acids
        (B) TYPE: amino acid
        (D) TOPOLOGY: linear (ii) MOLECULE TYPE: protein (xi) SEQUENCE DESCRIPTION: SEQ ID NO:3:

```
Met Val Tyr Glu Leu Ser Thr Cys Phe Phe Leu Cys Leu Leu Arg Phe
 1               5                  10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
                35                  40                  45

Phe Pro Pro Arg Val Pro Lys Ser Phe Pro Phe Asn Thr Ser Val Val
```

|  |  |  |  |  | 50 |  |  |  |  | 55 |  |  |  |  | 60 |  |  |  |  |
|---|---|---|---|---|---|---|---|---|---|---|---|---|---|---|---|---|---|---|---|---|

Tyr Lys Lys Thr Leu Phe Val Glu Phe Thr Val His Leu Phe Asn Ile
65                    70                        75                    80

Ala Lys Pro Arg Pro Pro Trp Met Gly Leu Leu Gly Pro Thr Ile Gln
                85                        90                    95

Ala Glu Val Tyr Asp Thr Val Val Ile Thr Leu Lys Asn Met Ala Ser
                    100                       105                   110

His Pro Val Ser Leu His Ala Val Gly Val Ser Tyr Trp Lys Ala Ser
                115                       120                   125

Glu Gly Ala Glu Tyr Asp Asp Gln Thr Ser Gln Arg Glu Lys Glu Asp
        130                       135                   140

Asp Lys Val Phe Pro Gly Gly Ser His Thr Tyr Val Trp Gln Val Leu
145                       150                   155                       160

Lys Glu Asn Gly Pro Met Ala Ser Asp Pro Leu Cys Leu Thr Tyr Ser
                    165                       170                   175

Tyr Leu Ser His Val Asp Leu Val Lys Asp Leu Asn Ser Gly Leu Ile
                180                       185                   190

Gly Ala Leu Leu Val Cys Arg Glu Gly Ser Leu Ala Lys Glu Lys Thr
        195                       200                   205

Gln Thr Leu His Lys Phe Ile Leu Leu Phe Ala Val Phe Asp Glu Gly
        210                       215                   220

Lys Ser Trp His Ser Glu Thr Lys Asn Ser Leu Met Gln Asp Arg Asp
225                       230                   235                       240

Ala Ala Ser Ala Arg Ala Trp Pro Lys Met His Thr Val Asn Gly Tyr
                    245                       250                   255

Val Asn Arg Ser Leu Pro Gly Leu Ile Gly Cys His Arg Lys Ser Val
                260                       265                   270

Tyr Trp His Val Ile Gly Met Gly Thr Thr Pro Glu Val His Ser Ile
        275                       280                   285

Phe Leu Glu Gly His Thr Phe Leu Val Arg Asn His Arg Gln Ala Ser
        290                       295                   300

Leu Glu Ile Ser Pro Ile Thr Phe Leu Thr Ala Gln Thr Leu Leu Met
305                       310                   315                       320

Asp Leu Gly Gln Phe Leu Leu Phe Cys His Ile Ser Ser His Gln His
                    325                       330                   335

Asp Gly Met Glu Ala Tyr Val Lys Val Asp Ser Cys Pro Glu Glu Pro
                340                       345                   350

Gln Leu Arg Met Lys Asn Asn Glu Glu Ala Glu Asp Tyr Asp Asp Asp
        355                       360                   365

Leu Thr Asp Ser Glu Met Asp Val Val Arg Phe Asp Asp Asn Ser
        370                       375                   380

Pro Ser Phe Ile Gln Ile Arg Ser Val Ala Lys Lys His Pro Lys Thr
385                       390                   395                       400

Trp Val His Tyr Ile Ala Ala Glu Glu Asp Trp Asp Tyr Ala Pro
                    405                       410                   415

Leu Val Leu Ala Pro Asp Asp Arg Ser Tyr Lys Ser Gln Tyr Leu Asn
                420                       425                   430

Asn Gly Pro Gln Arg Ile Gly Arg Lys Tyr Lys Lys Val Arg Phe Met
        435                       440                   445

Ala Tyr Thr Asp Glu Thr Phe Lys Thr Arg Glu Ala Ile Gln His Glu
        450                       455                   460

Ser Gly Ile Leu Gly Pro Leu Leu Tyr Gly Glu Val Gly Asp Thr Leu
465                       470                   475                       480

```
Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Pro Pro Val Leu Lys Arg
    770                 775                 780

His Gln Arg Glu Ile Thr Arg Thr Thr Leu Gln Ser Asp Gln Glu Glu
785                 790                 795                 800

Ile Asp Tyr Asp Asp Thr Ile Ser Val Glu Met Lys Lys Glu Asp Phe
            805                 810                 815

Asp Ile Tyr Asp Glu Asp Glu Asn Gln Ser Pro Arg Ser Phe Gln Lys
            820                 825                 830

Lys Thr Arg His Tyr Phe Ile Ala Ala Val Glu Arg Leu Trp Asp Tyr
            835                 840                 845

Gly Met Ser Ser Ser Pro His Val Leu Arg Asn Arg Ala Gln Ser Gly
    850                 855                 860

Ser Val Pro Gln Phe Lys Lys Val Val Phe Gln Glu Phe Thr Asp Gly
865                 870                 875                 880

Ser Phe Thr Gln Pro Leu Tyr Arg Gly Glu Leu Asn Glu His Leu Gly
            885                 890                 895

Leu Leu Gly Pro Tyr Ile Arg Ala Glu Val Glu Asp Asn Ile Met Val
            900                 905                 910
```

```
Thr Phe Arg Asn Gln Ala Ser Arg Pro Tyr Ser Phe Tyr Ser Ser Leu
        915                 920                 925
Ile Ser Tyr Glu Glu Asp Gln Arg Gln Gly Ala Glu Pro Arg Lys Asn
        930                 935                 940
Phe Val Lys Pro Asn Glu Thr Lys Thr Tyr Phe Trp Lys Val Gln His
945                 950                 955                 960
His Met Ala Pro Thr Lys Asp Glu Phe Asp Cys Lys Ala Trp Ala Tyr
                965                 970                 975
Phe Ser Asp Val Asp Leu Glu Lys Asp Val His Ser Gly Leu Ile Gly
                980                 985                 990
Pro Leu Leu Val Cys His Thr Asn Thr Leu Asn Pro Ala His Gly Arg
        995                 1000                1005
Gln Val Thr Val Gln Glu Phe Ala Leu Phe Phe Thr Ile Phe Asp Glu
        1010                1015                1020
Thr Lys Ser Trp Tyr Phe Thr Glu Asn Met Glu Arg Asn Cys Arg Ala
1025                1030                1035                1040
Pro Cys Asn Ile Gln Met Glu Asp Pro Thr Phe Lys Glu Asn Tyr Arg
                1045                1050                1055
Phe His Ala Ile Asn Gly Tyr Ile Met Asp Thr Leu Pro Gly Leu Val
        1060                1065                1070
Met Ala Gln Asp Gln Arg Ile Arg Trp Tyr Leu Leu Ser Met Gly Ser
        1075                1080                1085
Asn Glu Asn Ile His Ser Ile His Phe Ser Gly His Val Phe Thr Val
        1090                1095                1100
Arg Lys Lys Glu Glu Tyr Lys Met Ala Leu Tyr Asn Leu Tyr Pro Gly
1105                1110                1115                1120
Val Phe Glu Thr Val Glu Met Leu Pro Ser Lys Ala Gly Ile Trp Arg
                1125                1130                1135
Val Glu Cys Leu Ile Gly Glu His Leu His Ala Gly Met Ser Thr Leu
        1140                1145                1150
Phe Leu Val Tyr Ser Asn Lys Cys Gln Thr Pro Leu Gly Met Ala Ser
        1155                1160                1165
Gly His Ile Arg Asp Phe Gln Ile Thr Ala Ser Gly Gln Tyr Gly Gln
        1170                1175                1180
Trp Ala Pro Lys Leu Ala Arg Leu His Tyr Ser Gly Ser Ile Asn Ala
1185                1190                1195                1200
Trp Ser Thr Lys Glu Pro Phe Ser Trp Ile Lys Val Asp Leu Leu Ala
                1205                1210                1215
Pro Met Ile Ile His Gly Ile Lys Thr Gln Gly Ala Arg Gln Lys Phe
                1220                1225                1230
Ser Ser Leu Tyr Ile Ser Gln Phe Ile Ile Met Tyr Ser Leu Asp Gly
        1235                1240                1245
Lys Lys Trp Gln Thr Tyr Arg Gly Asn Ser Thr Gly Thr Leu Met Val
        1250                1255                1260
Phe Phe Gly Asn Val Asp Ser Ser Gly Ile Lys His Asn Ile Phe Asn
1265                1270                1275                1280
Pro Pro Ile Ile Ala Arg Tyr Ile Arg Leu His Pro Thr His Tyr Ser
                1285                1290                1295
Ile Arg Ser Thr Leu Arg Met Glu Leu Met Gly Cys Asp Leu Asn Ser
                1300                1305                1310
Cys Ser Met Pro Leu Gly Met Glu Ser Lys Ala Ile Ser Asp Ala Gln
                1315                1320                1325
Ile Thr Ala Ser Ser Tyr Phe Thr Asn Met Phe Ala Thr Trp Ser Pro
```

```
                   1330                        1335                        1340
Ser Lys Ala Arg Leu His Leu Gln Gly Arg Ser Asn Ala Trp Arg Pro
1345                1350                       1355                       1360

Gln Val Asn Asn Pro Lys Glu Trp Leu Gln Val Asp Phe Gln Lys Thr
                    1365                      1370                  1375

Met Lys Val Thr Gly Val Thr Thr Gln Gly Val Lys Ser Leu Leu Thr
                1380                      1385                1390

Ser Met Tyr Val Lys Glu Phe Leu Ile Ser Ser Ser Gln Asp Gly His
            1395                 1400                    1405

Gln Trp Thr Leu Phe Phe Gln Asn Gly Lys Val Lys Val Phe Gln Gly
        1410                1415                1420

Asn Gln Asp Ser Phe Thr Pro Val Val Asn Ser Leu Asp Pro Pro Leu
1425                1430                1435                       1440

Leu Thr Arg Tyr Leu Arg Ile His Pro Gln Ser Trp Val His Gln Ile
                1445              1450                    1455

Ala Leu Arg Met Glu Val Leu Gly Cys Glu Ala Gln Asp Leu Tyr
            1460              1465              1470
```

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CTTCCCATCC TGTCAGT                                                                          17

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CGCTTTCTCC CCAATCCAGC                                                                       20

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CTCACCCTAT TCCCATTCTC AGG                                                                   23

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CTCGTACTAC TCTTCAGTCA GA    22

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TACTATTTTA TTGCTGCAGT    20

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CTCCCCACAT GTTCTAAGA    19

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CTCCTTTACT CAGCCCTATA CCGTGGAGA    29

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CCTCTCGTCC CTATTCCTTC TATTCTAGC    29

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

TCCATTCTAT TCATTTCAGT    20

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

TTCTCCAGCC TCTACATCTC TCAGT                                               25

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TTCCTCATCT CCAGCAGT                                                        18

( 2 ) INFORMATION FOR SEQ ID NO:15:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CTCTCTTTTT CAGA                                                                  14

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CTCGCTACCT TCGAATTCAC CCCCAGA                                       27

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

TCACCTCTCC CTCCTCAGC                                                    19

( 2 ) INFORMATION FOR SEQ ID NO:18:

( i ) SEQUENCE CHARACTERISTICS:

(A) LENGTH: 147 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

```
AUUGAGGAAA AAUGGCAGGC AAUGUGGCAU GUCUGAAAAA GAGGAGGAAU GAUGGAGUGC      60

CUCAGAACUG CUUAAUGCAG GAGAGGUGCU GAGCUGAUUU CUUCCCUUUG AGGAAGAUAU     120

GUCAUAUGAAUC CAUUUUGAAU CAAAA                                          147
```